(12) United States Patent
Samaniego et al.

(10) Patent No.: US 10,271,964 B1
(45) Date of Patent: Apr. 30, 2019

(54) SYSTEM AND METHODS OF USE FOR PREPARING AND TESTING PRE-SUTURED TENDON CONSTRUCTS

(71) Applicant: Allosource, Centennial, CO (US)

(72) Inventors: Adrian C. Samaniego, Centennial, CO (US); Wendy Desiree Franklin, Westminster, CO (US); Sarah Song Yi Han, Aurora, CO (US); Jesse Compton, Littleton, CO (US); Marina Bull, Westminster, CO (US)

(73) Assignee: Allosource, Centennial, CO (US)

( * ) Notice: Subject to any disclaimer, the term of this patent is extended or adjusted under 35 U.S.C. 154(b) by 0 days.

(21) Appl. No.: 15/880,959

(22) Filed: Jan. 26, 2018

(51) Int. Cl.
| | |
|---|---|
| *G01L 5/00* | (2006.01) |
| *A61F 2/46* | (2006.01) |
| *G01L 5/06* | (2006.01) |
| *G01L 1/04* | (2006.01) |
| *A61F 2/08* | (2006.01) |

(52) U.S. Cl.
CPC .......... *A61F 2/4644* (2013.01); *A61F 2/4657* (2013.01); *G01L 1/04* (2013.01); *G01L 5/06* (2013.01); *A61F 2/08* (2013.01); *A61F 2002/4666* (2013.01)

(58) Field of Classification Search
CPC .. A61F 2/4644; A61F 2/08; A61F 2002/4666; G01L 1/04; G01L 5/06
USPC ...................................................... 73/862.42
See application file for complete search history.

(56) References Cited

U.S. PATENT DOCUMENTS

| | | | |
|---|---|---|---|
| 8,298,284 B2 | 10/2012 | Cassani | |
| 9,504,557 B1 * | 11/2016 | Samaniego | ............... A61F 2/08 |
| 2006/0271192 A1 * | 11/2006 | Olsen | .................... A61F 2/0811 623/13.14 |
| 2007/0239275 A1 | 10/2007 | Willobee | |
| 2011/0071508 A1 * | 3/2011 | Duval | ................ A61B 1/00087 606/1 |
| 2012/0046746 A1 | 2/2012 | Konicek | |
| 2013/0116730 A1 | 5/2013 | Denham et al. | |
| 2014/0277020 A1 | 9/2014 | Koogle et al. | |
| 2015/0313705 A1 * | 11/2015 | Euteneuer | ............. A61F 2/0063 623/13.14 |
| 2016/0113758 A1 * | 4/2016 | Diduch | ................. A61F 2/0811 606/232 |
| 2017/0127911 A1 * | 5/2017 | Yamamoto | ........... A61B 1/0052 |

* cited by examiner

*Primary Examiner* — Max H Noori
(74) *Attorney, Agent, or Firm* — James A. Sheridan; Sheridan Law, LLC

(57) ABSTRACT

There is disclosed a customizable system and methods of use for manufacturing and testing a variety of pre-sutured allograft tendon constructs sutured according to a variety of stitching patterns and featuring a variety of tissue lengths and types. One embodiment includes a triple-channel base having first, second, and third longitudinal channels extending between first and second ends of the base, as well as a plurality of tendon-manipulation accessories. Each of the tendon-manipulation accessories includes a locking-base assembly for selectively securing the accessory to the base such that the multiple tendon-manipulation accessories may be secured to the triple-channel base in a variety of custom arrangements suitable for preparing the variety of pre-sutured constructs and/or for pre-tensioning or testing the variety of the pre-sutured constructs. Other embodiments are also disclosed.

20 Claims, 33 Drawing Sheets

SYSTEM AND METHODS OF USE FOR PREPARING AND TESTING PRE-SUTURED TENDON CONSTRUCTS

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from cadaveric donor-derived, living-related, or living-unrelated donors and can help patients regain mobility, restore function, enjoy a better quality of life, and even save lives in the case of cardiovascular tissue or skin.

When a ligament or tendon becomes detached from the bone, surgery is usually required to re-secure the ligament or tendon. Often, a substitute allograft ligament or tendon (hereinafter an "allograft construct" or "allograft tendon construct") is attached to the bone to facilitate regrowth and permanent attachment. The reattachment procedure involves drilling a bone tunnel between two bones such as, for example, the tibia and the femur, and securing the allograft construct within the tunnel.

Traditionally, surgeons have been responsible for tendon graft preparation, individually preparing an appropriately cross-sectioned, whip-stitched tendon for each patient and/or circumstance in the operating theatre. Recently, pre-sutured allograft tendon constructs have become available from third-party providers, such as, for example, allograft processing centers, thereby allowing surgeons to order high quality, consistent, strong, and sterile pre-sutured tendon constructs, either individually or as part of a larger "kit" carrying a variety of pre-sutured construct sizes.

Pre-sutured tendon constructs are oftentimes pre-tensioned prior to fixation between the anchoring bones of the recipient to evaluate the integrity of the constructs and to ensure that each pre-sutured tendon construct is prepared based on a "book" value of tension force, rather than simply by "feel," which is generally the case with surgeons who prepare tendon constructs in the operating theatre.

Existing tooling setups for pre-suturing and pre-tensioning or testing tendon constructs are generally oversized, cumbersome, non-customizable and configured for only a specific suturing method and/or tissue or construct type, and are further ill-suited for use in a clean room environment and for sterilization in an autoclave or other sterilizing processor.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a customizable system for manufacturing and testing a pre-sutured tendon construct. The system may comprise (1) a base having first, second, and third longitudinal channels extending between first and second ends of the base; and (2) a plurality of tendon-manipulation accessories, each having a locking base assembly for selectively securing each of the tendon-manipulation accessories along one of the first, the second, or the third longitudinal channels so as to configure two or more of the tendon-manipulation accessories in two or more custom arrangements suitable for each of preparing the pre-sutured tendon construct and pre-tensioning the pre-sutured tendon construct.

Another embodiment provides a soft-tissue construct preparation and testing tool, comprising: (1) a triple-channel base extending longitudinally between a first end and a second end; (2) a pulley-tension assembly having a pulley secured at a first longitudinal position within a second channel of the triple-channel base; (3) a tension-hook assembly secured at a second longitudinal position within a first channel of the triple-channel base; and (4) a post assembly secured at the second longitudinal position within a third channel of the triple-channel base, wherein: (a) a pre-sutured soft-tissue construct extends from a first end attached to the post assembly, about the pulley of the pulley-tension assembly, to a second end attached to the tension-hook assembly; (b) increasing a distance between the first and the second longitudinal positions increases a tension placed upon the pre-sutured soft-tissue construct and registers a proportional tension-force measurement on the tension-hook assembly; and (c) a distance between the first and the second ends of the triple-channel base is less than a distance between the first and the second ends of the pre-sutured soft-tissue construct.

Yet another embodiment provides a method of preparing and pre-tensioning a pre-sutured tendon construct. The method may include the steps of (1) aseptically assembling a customizable pre-sutured construct system having a triple-channel base and a plurality of tendon-manipulation accessories into a first custom arrangement in which at least two of the tendon-manipulation accessories are secured upon the triple-channel base in a manner suitable for preparing a first pre-sutured tendon construct; (2) securing a first tendon portion between the at least two tendon-manipulation accessories of the first custom arrangement; (3) suturing the first tendon portion according to a first stitching pattern to form the first pre-sutured tendon construct; (4) removing the first pre-sutured tendon construct from the first custom arrangement; (5) removing the at least two tendon-manipulation accessories from the triple-channel base; (6) aseptically assembling the customizable pre-sutured construct system into a second custom arrangement in which at least another two of the plurality of the tendon-manipulation accessories are secured upon the triple-channel base in a manner suitable for preparing a second pre-sutured tendon construct; (7) securing a second tendon portion between the at least another two of the plurality of the tendon-manipulation accessories of the second custom arrangement; (8) suturing the second tendon portion according to a second stitching pattern to form the second pre-sutured tendon construct; and (9) removing the second pre-sutured tendon construct from the second custom arrangement.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
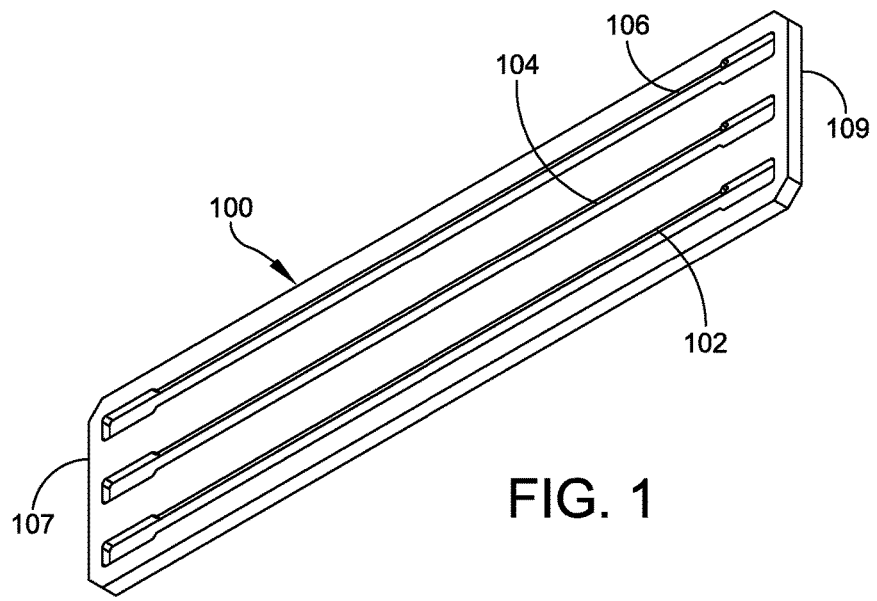
FIG. 1 illustrates a perspective view of one embodiment of a triple-channel base of a customizable system for preparing and testing pre-sutured tendon constructs.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to the efficient and effective preparation and pre-tensioning, or testing, of a variety of pre-sutured tendon or other soft-tissue constructs (hereinafter "pre-sutured tendon constructs" or "pre-sutured constructs") such as, for example, lateral Achilles tendon constructs, pre-sutured fascia rolls, or any soft-tissue/tendon constructs that require holding a tendon or other soft-tissue portion in place during suturing under a specified tension, as well as subsequent testing of the integrity of the prepared pre-sutured construct.

As discussed above in the Background section, existing tooling setups are generally configured for preparation of constructs according to one particular suturing method and/or one particular tissue or construct type or for the testing of one particular suturing method and/or one particular tissue or construct type. In this regard, a dedicated and oftentimes cumbersome tooling setup is currently needed for preparation according to each of the different suturing methods and/or construct types, and further tooling setups are currently required for construct pre-tensioning, or tension testing, of each different construct type, resulting in the need for multiple equipment setups to accomplish the preparation and testing of a variety of tendon constructs prepared according to different stitching patterns or using a variety of tissue samples of varying types and/or lengths and sizes. These redundancies waste valuable clean-room real estate and complicate already intricate processes.

In addition to equipment redundancies, existing construct preparation equipment setups are configured for specific tissue specimens and require the use of a premium tissue supply, or are only able to utilize the most intact tissue specimens available for construct preparation. Because the setups are not adjustable or customizable, these existing setups render tissue specimens that fail pre-established length requirements, to which the existing setups cater, both unusable and underutilized.

Moreover, existing tooling setups have not been designed with an eye toward space savings, material savings, and personnel efficiency. Oftentimes, tooling setups are oversized to accommodate pre-sutured constructs of above average length, rendering them ill-suited for use in the limited clean room environment and difficult or impossible to sterilize in an autoclave or other traditional sterilizing processor. Further, many equipment setups are not designed for use by a single individual. A preparing technician or another personnel member oftentimes requires assistance from an additional individual in preparing and/or testing a pre-sutured construct.

Embodiments of the customizable system for manufacturing and testing a pre-sutured tendon construct disclosed herein are designed to address the particular challenges currently presented in the allograft industry, with improved functionality that allows a single technician to efficiently prepare and then test a variety of different pre-sutured construct types and sizes using the same customizable tool, which may be aseptically customized within the clean-room environment to accommodate each construct length, suturing method, tissue type or length, and/or construct type, thereby providing a multi-use tool that allows for the production of pre-sutured tendon constructs using human tissue materials that would otherwise be discarded. The customizable system may then be sterilized using sterilization equipment already present within the clean-room environment.

One embodiment of the customizable pre-sutured construct preparation and testing system includes a base (FIGS. 1-3) and a plurality of tendon-manipulation accessories (FIGS. 4-22), each designed to be selectively secured within one or more longitudinal channels formed within the triple-channel base such that the accessories may be selectively configured in a variety of custom arrangements to hold tendon portions as necessary during the pre-sutured construct preparation process and to apply tension to completed pre-sutured constructs to test the integrity of the assembled tendon constructs prior to insertion in a surgical environment.

Figure 2:
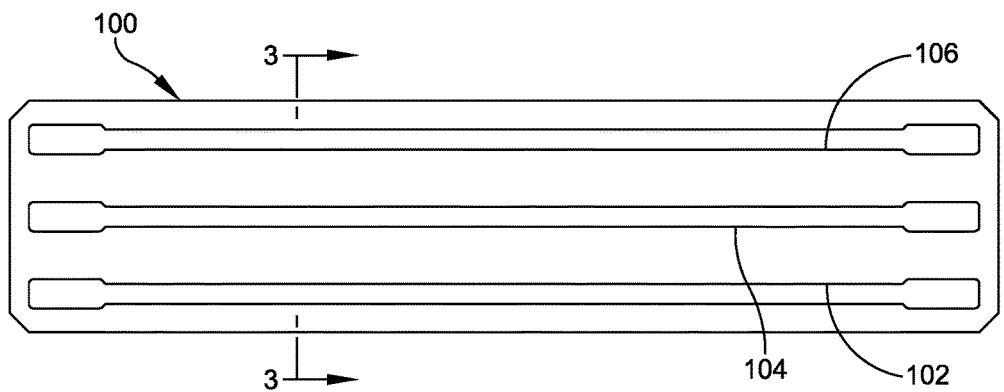
FIG. 2 illustrates a top plan view of the triple-channel base of FIG. 1.
Figure 3:
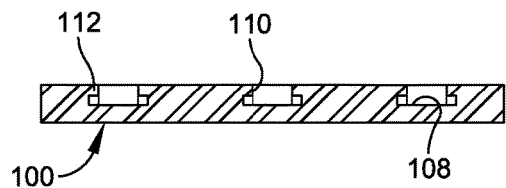
FIG. 3 illustrates a cross-sectional view of the triple-channel base of FIG. 1.

Turning to exemplary embodiments, FIGS. 1-3 illustrate respective perspective, top-plan, and cross-sectional views of one embodiment a triple-channel base 100, which serves as an anchor for the plurality of the tendon-manipulation accessories described below in relation to FIGS. 4-22. In this embodiment, the base 100 may form first, second, and third longitudinal channels 102, 104, 106 that extend between a first end 107 and a second end 109 of the base 100. Each of the first, the second, and the third channels 102, 104, 106 may include a bed portion 108 and a neck portion 110 that combine to form a lip 112 that is leveraged in securing the various tendon-manipulation accessories at desired positions along the channels 102, 104, 106, as discussed below. Embodiments of the triple-channel base 100 may be formed of stainless steel and/or an autoclavable or otherwise sterilizable plastic.

Figure 4:
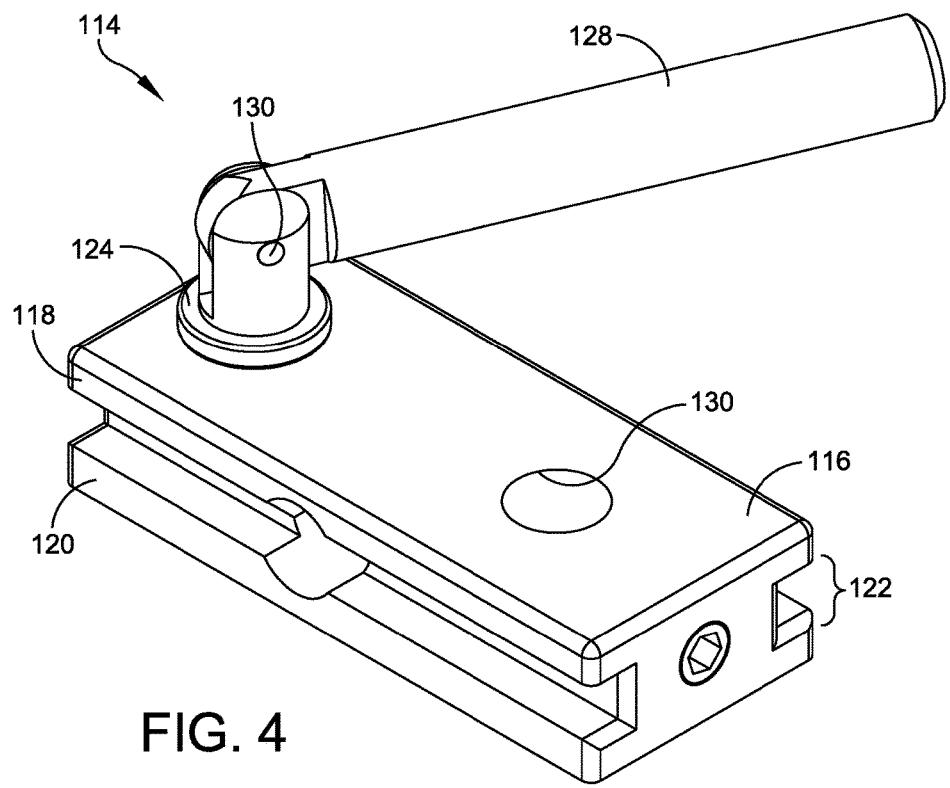
FIG. 4 illustrates a perspective view of one embodiment of a locking-base assembly for use with a plurality of tendon-manipulation accessories of a customizable system for preparing and testing pre-sutured tendon constructs.
Figure 5:
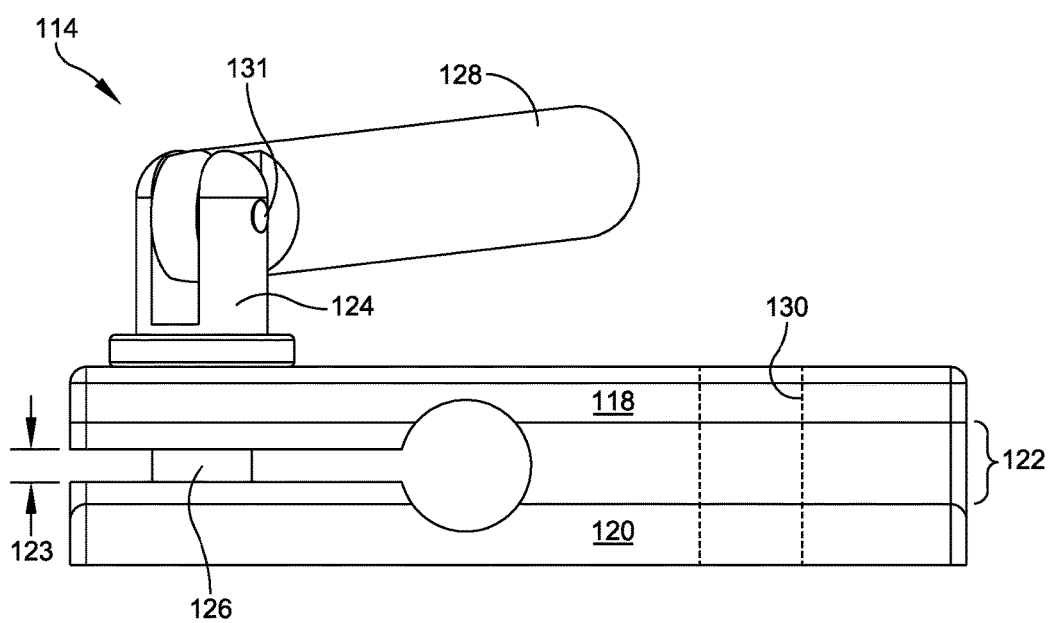
FIG. 5 illustrates a side view of the locking-base assembly of FIG. 4.

FIGS. 4-5 illustrate respective perspective and side plan views of one embodiment of a locking-base assembly 114, which may form the base or anchor of each of the tendon-manipulation accessories discussed below in relation to FIGS. 6-22 and be used to selectively secure each of the accessories within the first, the second, or the third longitudinal channels 102, 104, 106 of the base 100. In this embodiment, the locking-base assembly 114 may include a lock base 116 having a top plate 118 and a bottom plate 120 that form a c-channel 122 along each longitudinal side of the lock base 116. When placed within one of the first, the second, or the third channels 102, 104, 106, the lip 112 of the channel 102, 104, 106 glides within the c-channel 122 of the lock base 116, thereby allowing the lock base 116 to glide back and forth within the channel 102, 104, 106 to a desired longitudinal position between the first and the second ends 107, 109 of the base 100.

To secure the lock base 116 at the desired longitudinal position within the selected channel 102, 104, 106, the locking-base assembly 114 may also include an offset 123 that separates a portion of the top and the bottom plates 118, 120. The locking-base assembly 114 may further include a swivel 124 having a threaded portion 126 that extends through the top plate 118, across the offset 123, and into the bottom plate 120. A handle 128 may be rotatably coupled with the swivel 124 via a hinge pin 131. In use, the technician or operator may slide the lock base 116 to the desired longitudinal position within the selected longitudinal channel 102, 104, 106, before using the handle 128 to rotate/tighten the swivel 124, causing the top and the bottom plates 118, 120 to move toward one another, or to clamp down upon the lip 112 of the channel and secure the locking-base assembly 114 at the desired longitudinal position within the selected channel 102, 104, 106. The top and the bottom plates 118, 120 may also form a thru-hole or threaded insertion aperture 130 for receiving and retaining a post or other insertion hardware of an attached tendon-manipulation accessory, as detailed below.

Figure 6:
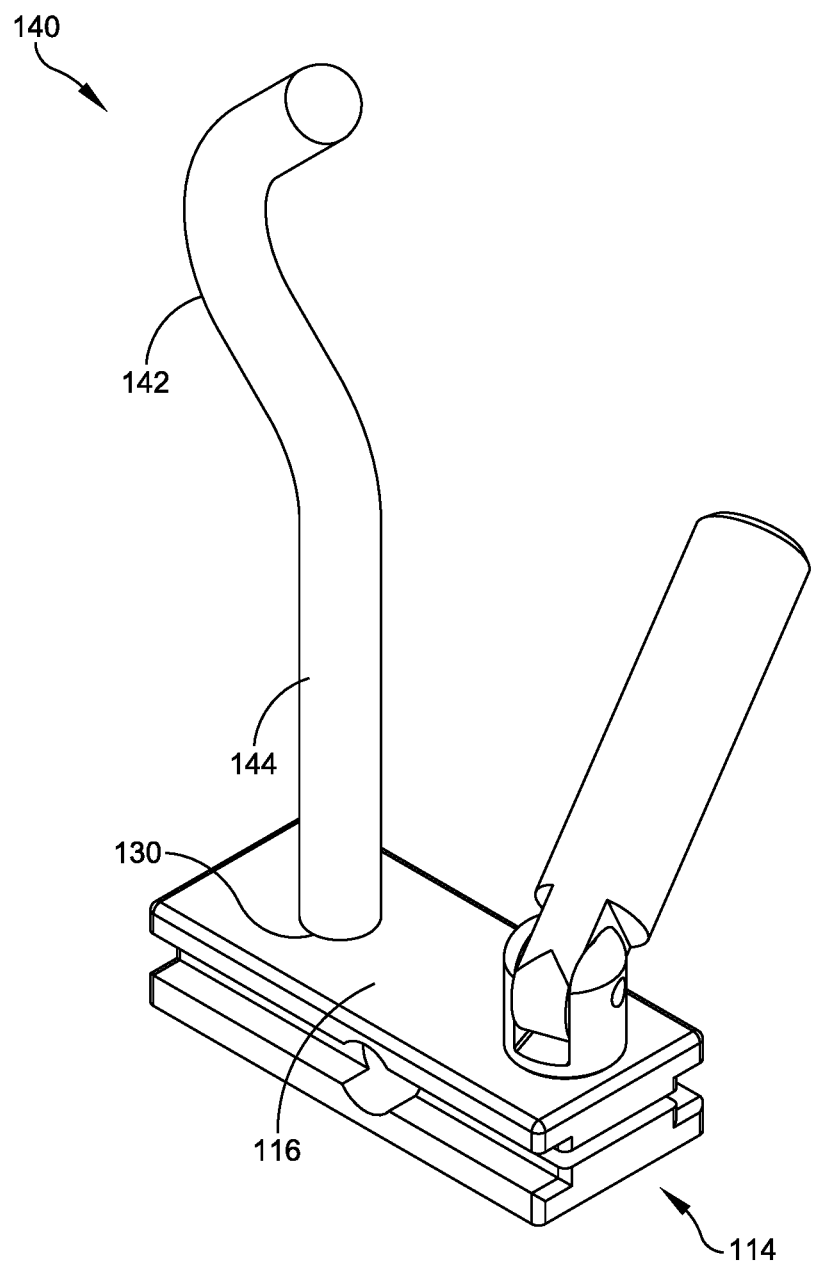
FIG. 6 illustrates a perspective view of a holder assembly for selectively securing to the triple-channel base of FIG. 1.

Turning to a variety of exemplary tendon-manipulation accessories for selective fixation upon the triple-channel base 100, FIG. 6 illustrates a perspective view of one embodiment of a holder assembly 140. In this embodiment, the holder assembly 140 may include a holder hook 142 either affixed to or incorporated into a post 144 that is inserted into the insertion aperture 130 of the lock base 116 of the locking-base assembly 114. The post 144 may be inserted into the insertion aperture 130 via a threaded coupling, a press fit, or via any other appropriate insertion method. The holder hook 142 may take any appropriate size, shape, type, and/or configuration that renders the holder hook 142 suitable as a soft-tissue return or a suture return or tie-off point.

Figure 7:
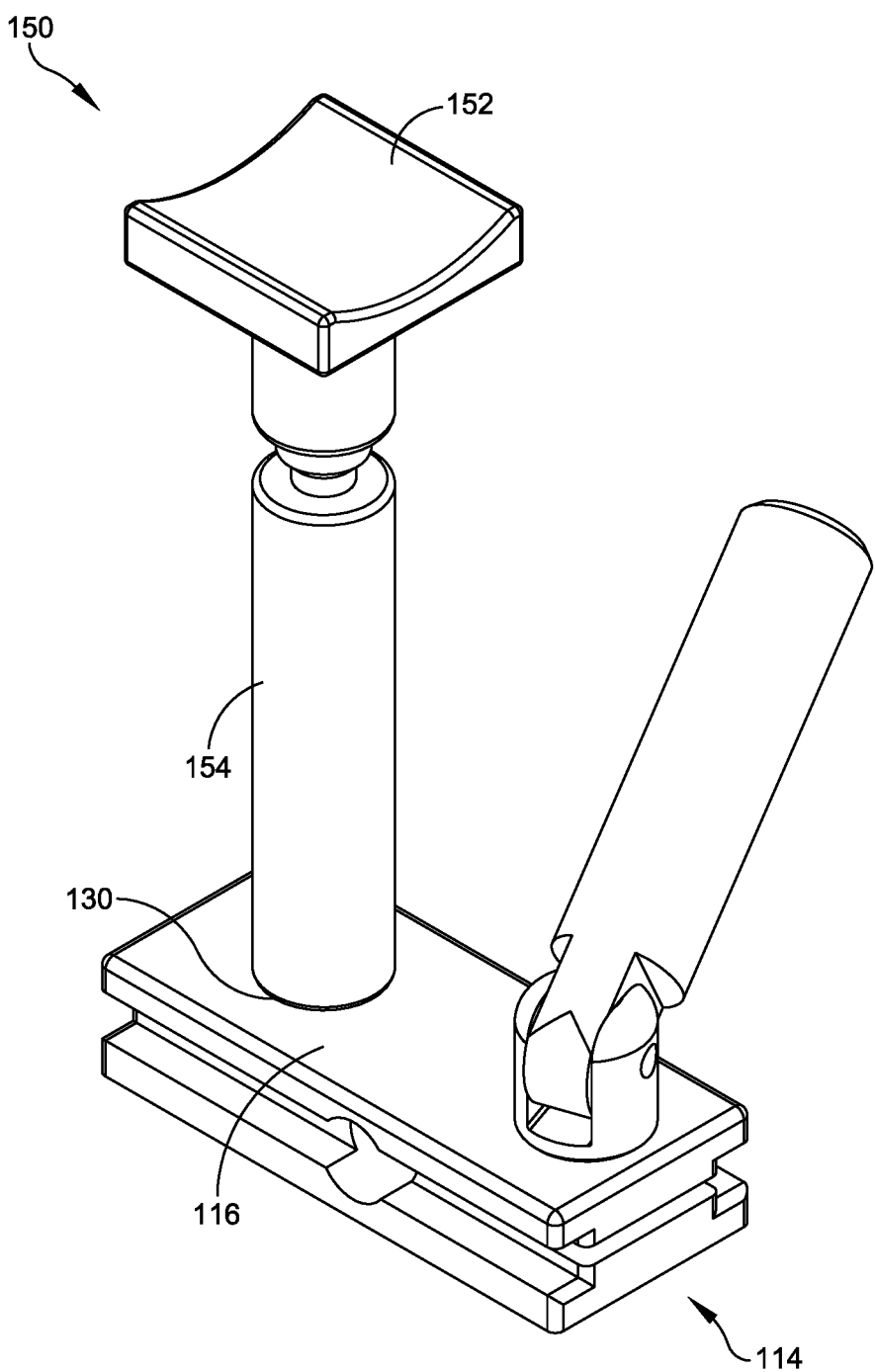
FIG. 7 illustrates a perspective view of a saddle assembly for selectively securing to the triple-channel base of FIG. 1.

FIG. 7 illustrates a perspective view of one embodiment of a saddle assembly 150. In this embodiment, the saddle assembly 150 may include a rest or a saddle 152 either affixed to or incorporated into a post 154, which is, in turn, inserted into the insertion aperture 130 of the locking base 116 in any appropriate manner. In one embodiment, the saddle 152 may be rotatively coupled with the post 154 such that the saddle/rest 152 may be positioned at a desired angle relative to the locking-base assembly 114 and the base 100, and therefore, relative to the other tendon-manipulation accessories positioned upon the base 100 so as to receive and support a tendon specimen portion or a construct portion at an appropriate angle as part of a custom arrangement of tendon-manipulation accessories upon the base 100.

Figure 8:
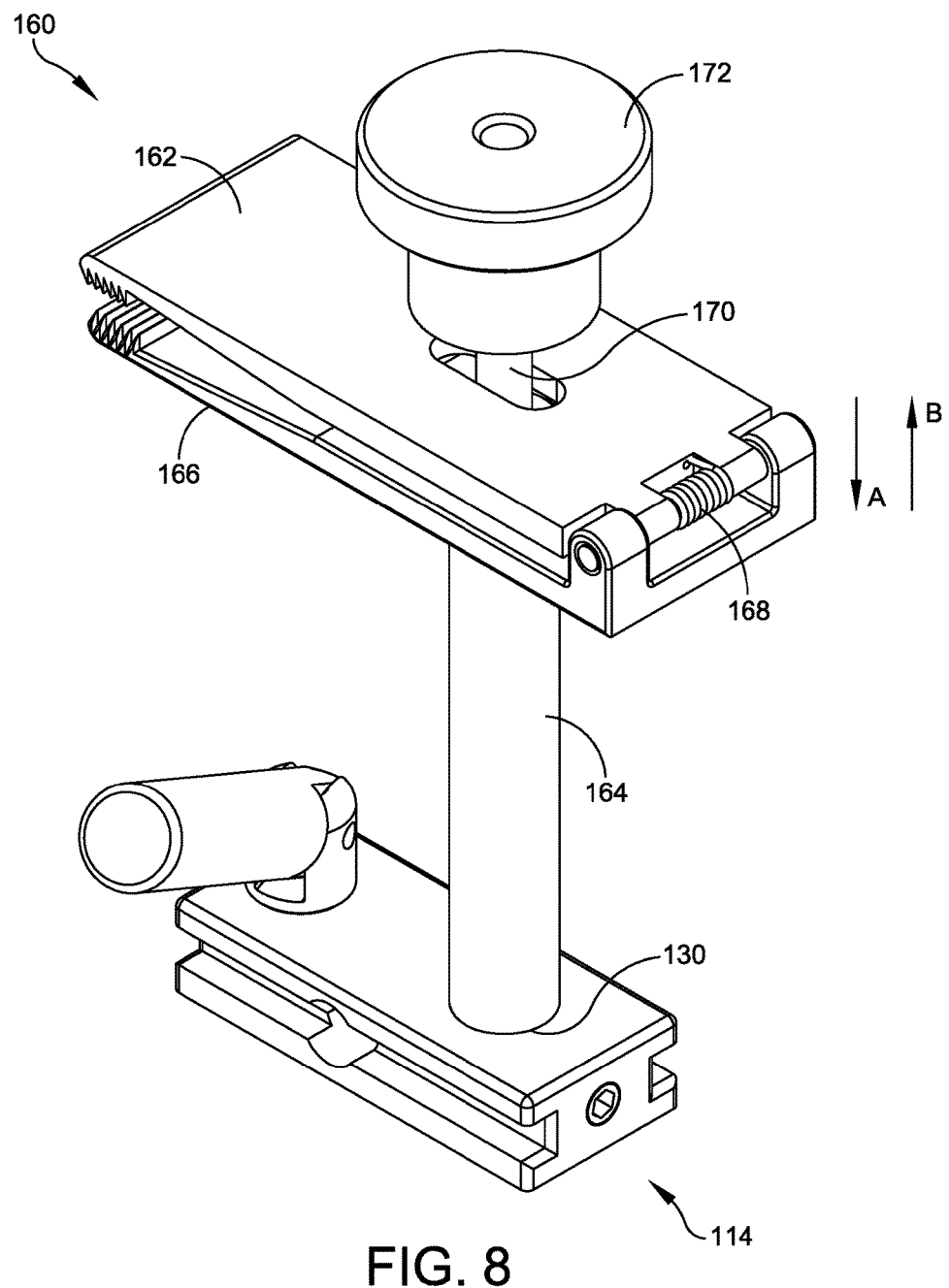
FIG. 8 illustrates a perspective view of horizontal tendon-clamp assembly for selectively securing to the triple-channel base of FIG. 1.

FIG. 8 illustrates a perspective view of one embodiment of a horizontal tendon-clamp assembly 160. In this embodiment, the horizontal tendon-clamp assembly 160 may include an upper jaw 162 that is hingedly coupled with a lower jaw 166 via a torsion spring 168, which is biased toward an open position of the upper and the lower jaws 162, 166, as shown in FIG. 8. The lower jaw 166 may be affixed to or about a post 164 that is, in turn, affixed to the locking-base assembly 114 via the insertion aperture 130 according to any appropriate fixation method. A threaded stud 170 having a knob 172 at its proximal end may be threaded into the post 164, such that when the knob 172 rotated in a first direction, the threaded stud 170 translates downward into the post 164 in the direction of arrow A, thereby causing the knob 172 to translate downward in the direction of arrow A to compress the upper jaw 162 against the lower jaw 166 in a closed position in which a tendon portion may be clamped. Rotating the knob 172 in a second direction causes the threaded stud 170 to translate upward out of the post 164 in the direction of arrow B, thereby translating the knob 172 in the direction of arrow B and releasing the upper jaw 162 back to the open position in which the tendon portion is released.

Figure 9:
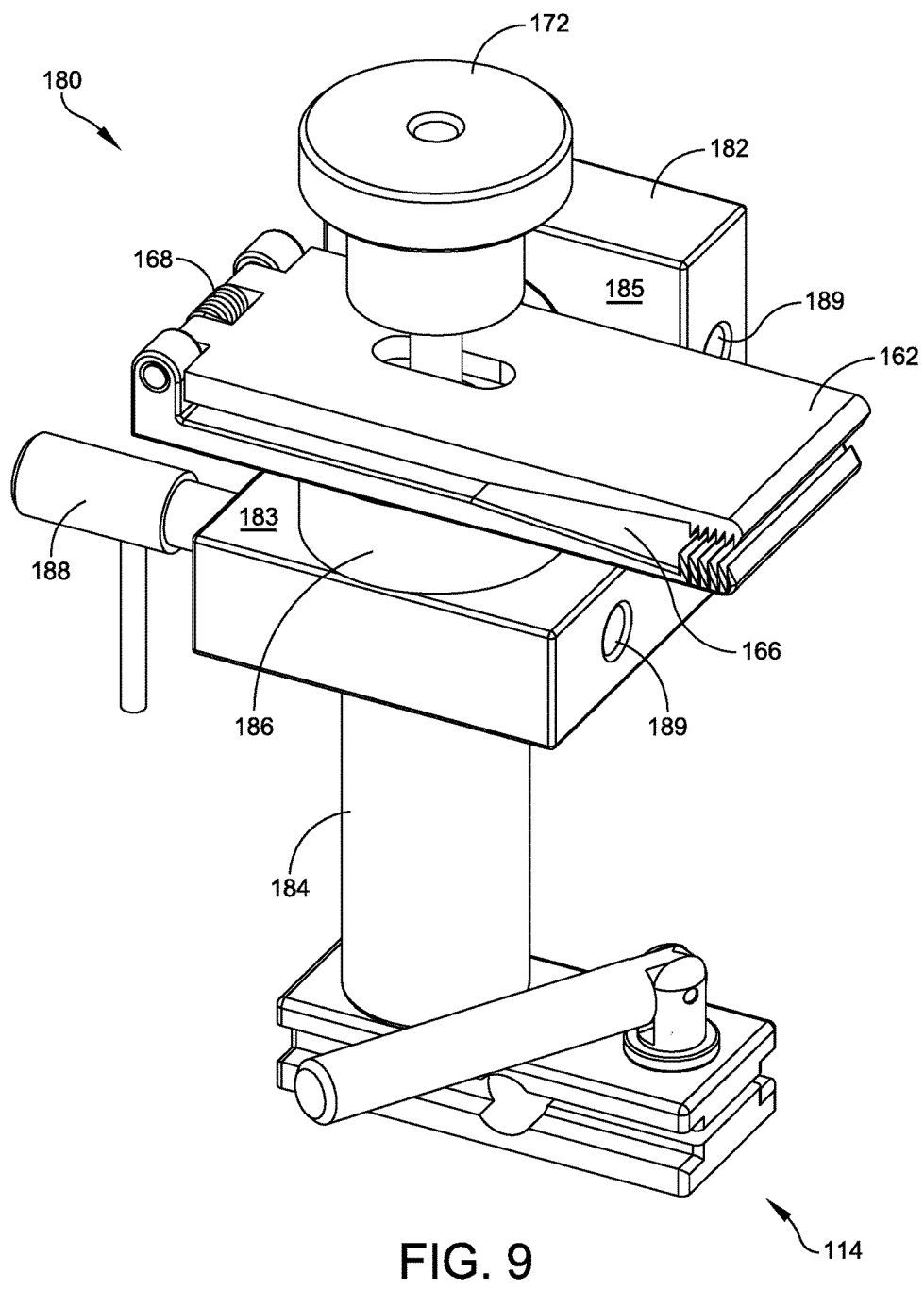
FIG. 9 illustrates a perspective view of a dual-direction tendon-clamp assembly for selectively securing to the triple-channel base of FIG. 1, in a horizontal configuration.
Figure 10:
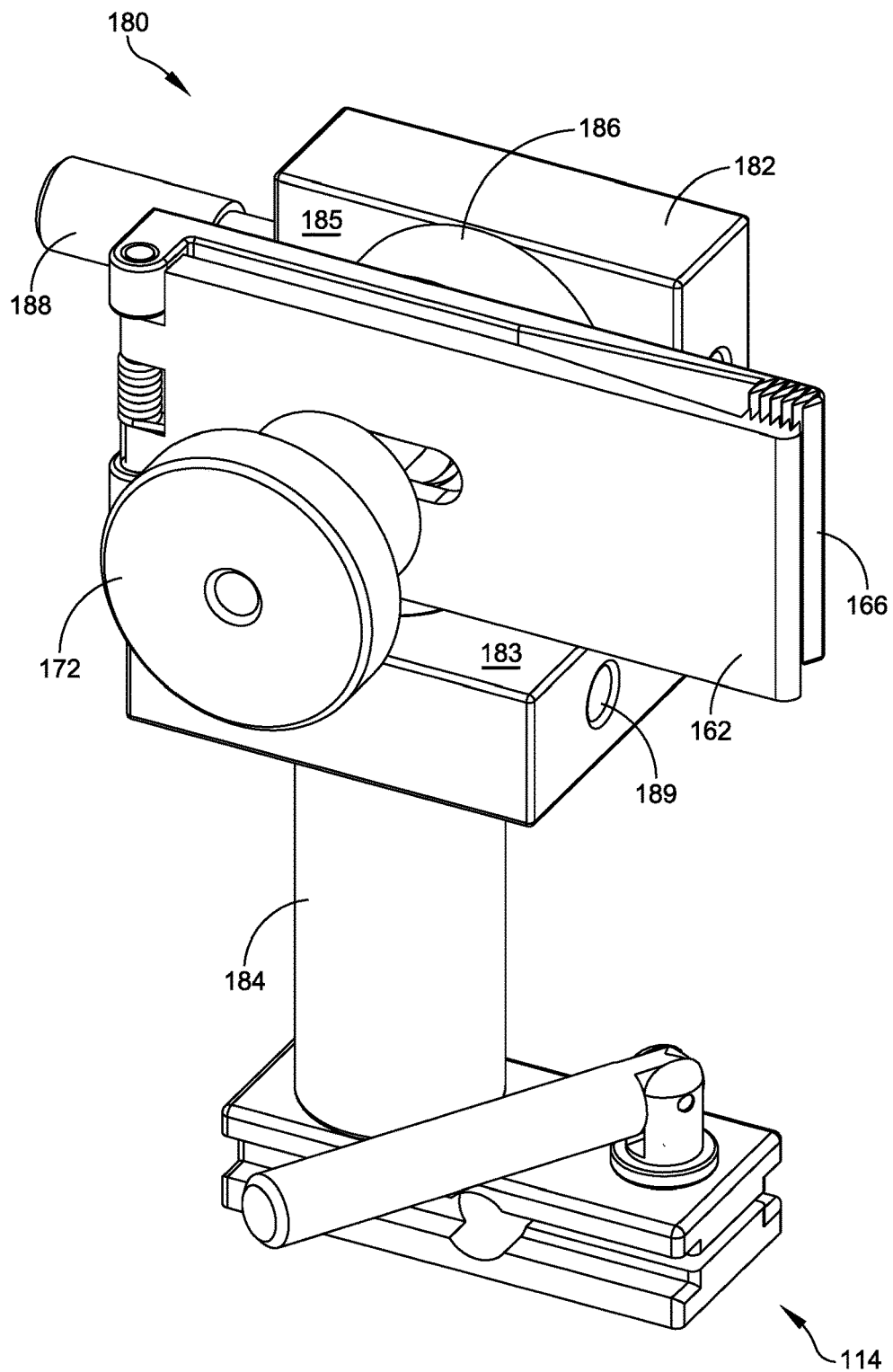
FIG. 10 illustrates a perspective view of the dual-direction tendon-clamp assembly of FIG. 9, in a vertical configuration.
Figure 11:
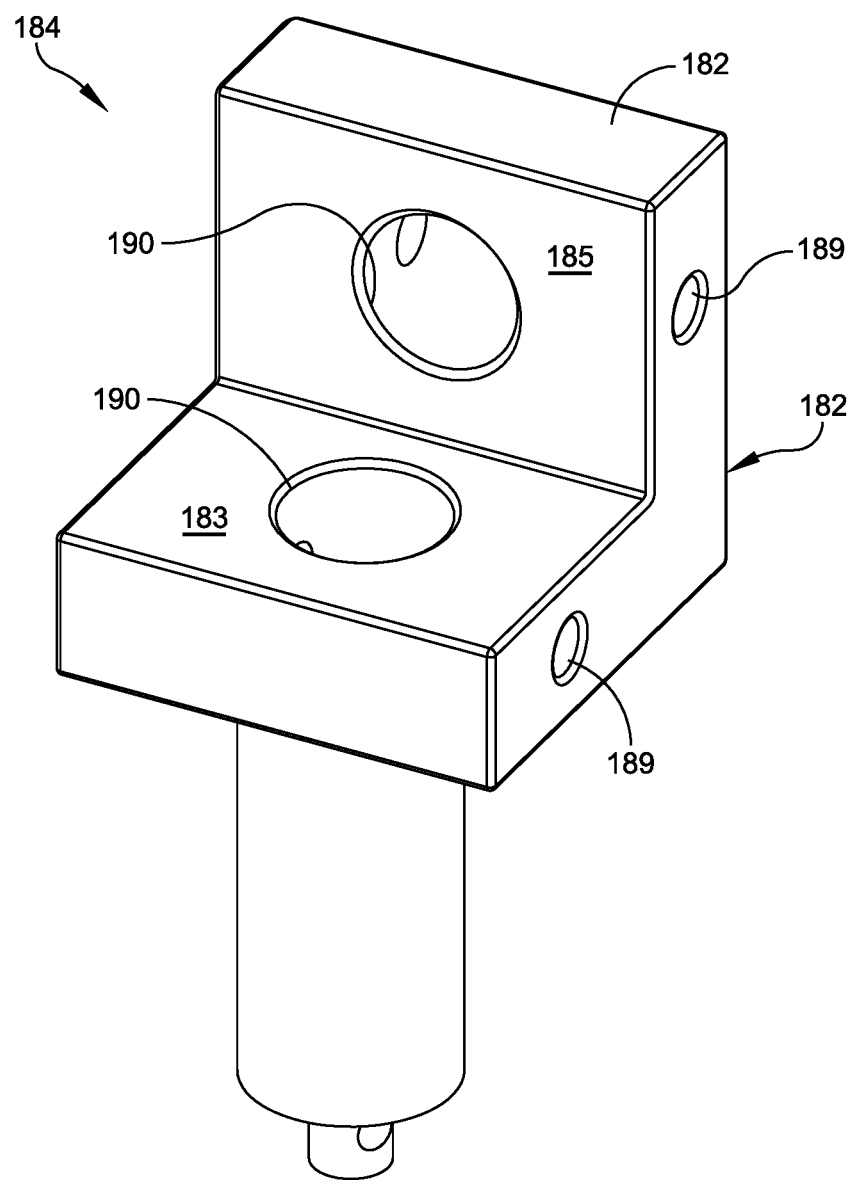
FIG. 11 illustrates a perspective view of a dual-direction post of the dual-direction tendon-clamp assembly of FIG. 9.

FIGS. 9-10 illustrate perspective views of one embodiment of a dual-direction tendon-clamp assembly 180 assembled in horizontal and vertical configurations, respectively. In this embodiment, the dual-direction tendon-clamp assembly 180 may be similar to and share several components of the horizontal tendon-clamp assembly 160, with the exception of a dual-direction post 184, which may be affixed to the locking-base assembly 114 via the insertion aperture 130, as well as a threaded receiver 186 and a plunger 188. FIG. 11 details one embodiment of the dual-direction post 184, which may include a dual-direction block 182 having a horizontal platform 183 and a vertical platform 185. Each of the horizontal and the vertical platforms 183, 185 may include a threaded thru-hole 189 and a receiver aperture 190.

The lower jaw 166 of the dual-direction tendon-clamp assembly 180 may be affixed to the threaded receiver 186 in any appropriate manner. Thus, the threaded receiver 186 and the hinged jaws 162 and 166 may be attached to the dual-direction block 182 in a horizontal configuration, shown in FIG. 9, or in a vertical configuration, shown in FIG. 10, by attaching the threaded receiver 186 to either the horizontal platform 183 or the vertical platform 185 of the dual-direction block 182, respectively. This attachment of the threaded receiver 186, and thus the hinged jaws 162, 166, to the horizontal and the vertical platforms 183, 185 may occur via the plunger 188, which may threadably engage with the appropriate threaded thru-hole 189 that extends through each of the platforms 183, 185. In one embodiment, the plunger 188 may be rotatively inserted into the thru-hole 189 until it interferes or engages with a portion or a surface of the receiver 186, as inserted into the receiver aperture 190.

Once assembled in the horizontal or the vertical configuration, the upper and the lower jaws 162, 166 of the dual-direction tendon clamp assembly 180 may be moved between open and closed positions to grip or clamp a tendon portion in a similar manner as the horizontal clamp assembly 160 of FIG. 8, or by rotating the knob 172 in first and second directions to move the upper jaw 162 toward and away from the lower jaw 166.

Figure 12:
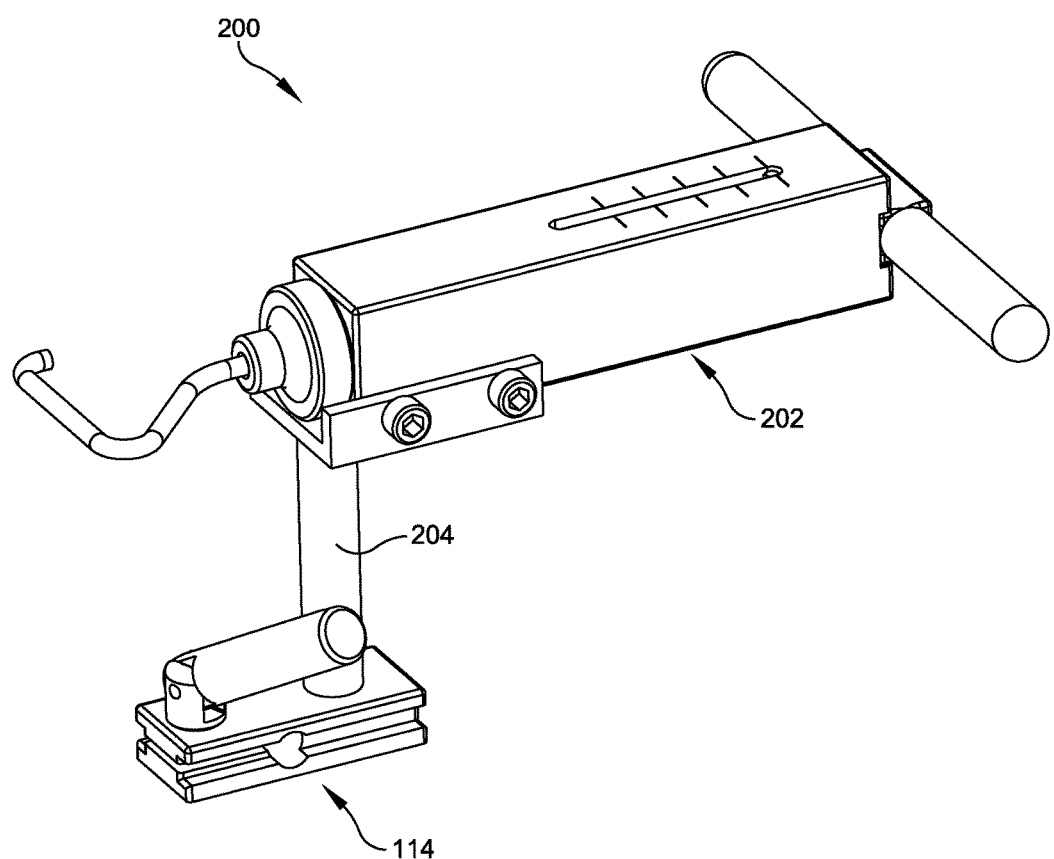
FIG. 12 illustrates a perspective view of one embodiment of a tall tension-hook assembly for selectively securing to the triple-channel base of FIG. 1.

FIG. 12 illustrates a perspective view of one embodiment of a tall tension-hook assembly 200. In this embodiment, the tall tension-hook assembly 200 may include a tensioner cradle assembly 202 mounted upon the locking-base assembly 114 via a post 204 that is inserted into the insertion aperture 130 of the locking-base assembly 114.

Figure 13:
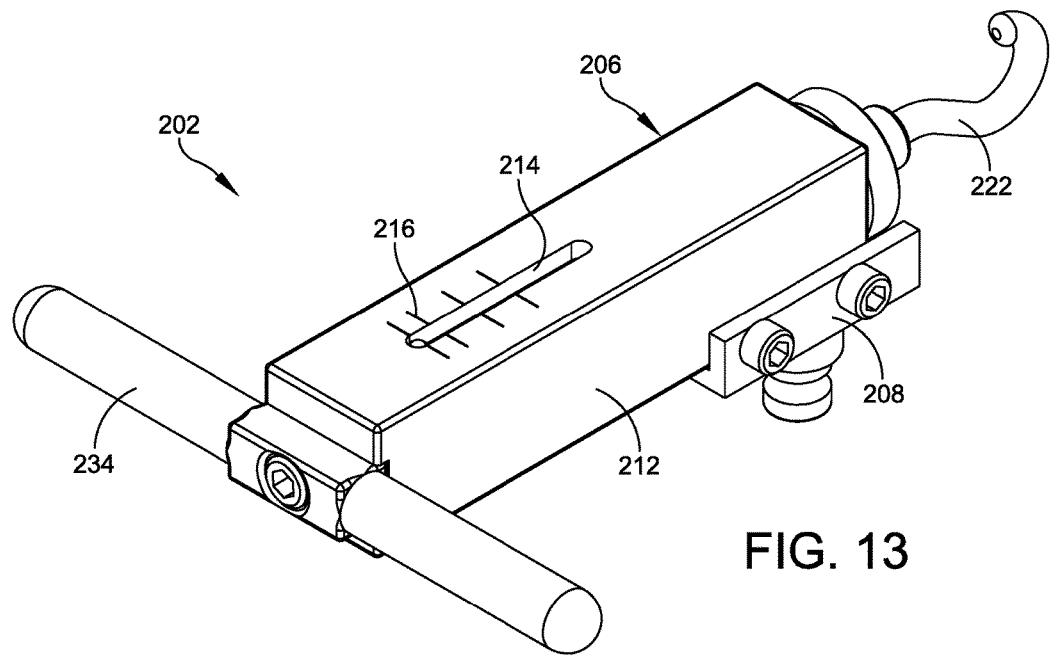
FIG. 13 illustrates a perspective view of one embodiment of a tensioner cradle assembly of the tall tension-hook assembly of FIG. 12.
Figure 14:
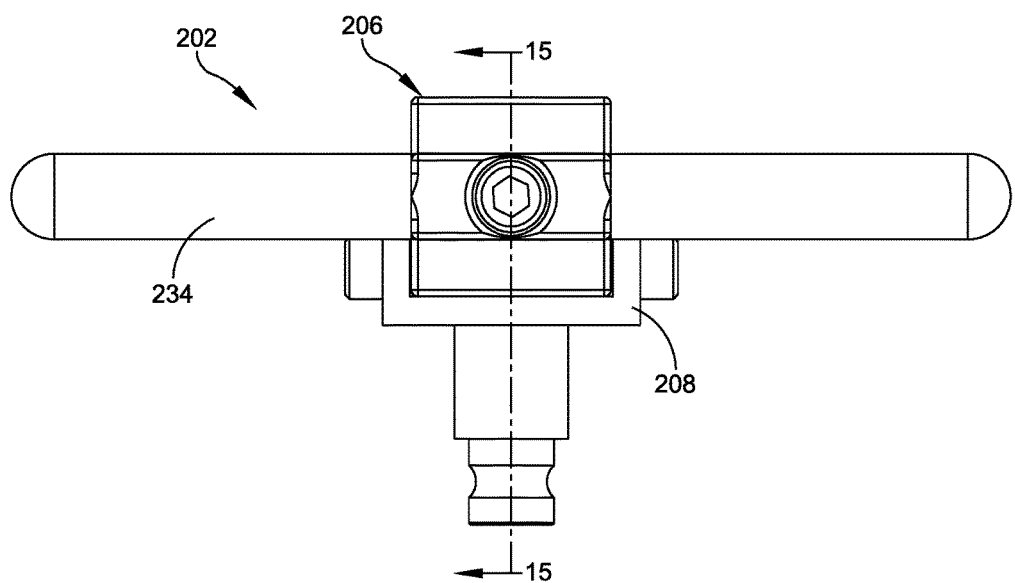
FIG. 14 illustrates an end view of the tensioner cradle assembly of FIG. 13.
Figure 15:
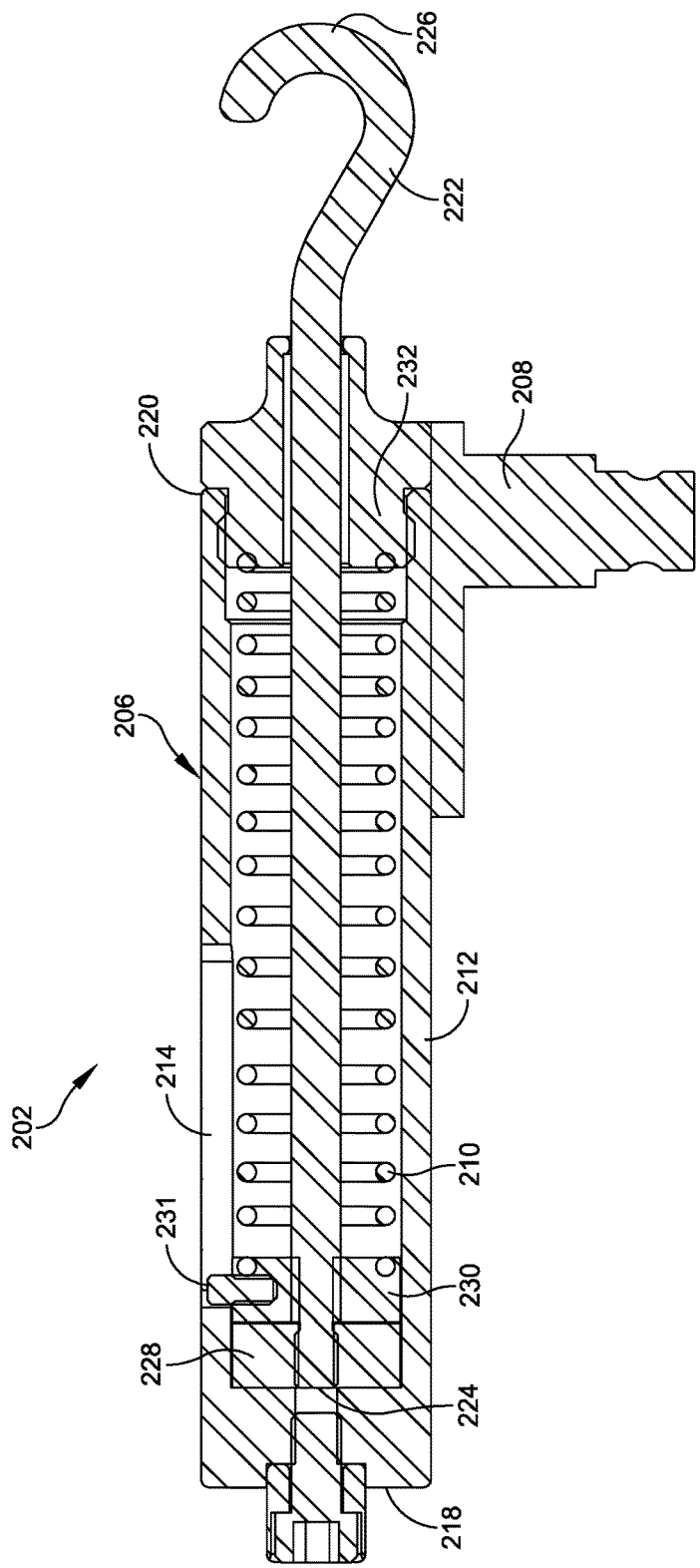
FIG. 15 illustrates a cross-sectional view of the tensioner cradle assembly of FIG. 13.

FIGS. 13-15 illustrate perspective, end, and cross-sectional views of one embodiment of the tensioner cradle assembly 202, respectively. In this embodiment, the tensioner cradle assembly 202 may include a hook-actuated force gauge 206 disposed upon and affixed to a cradle 208 configured for attachment to the post 204 (FIG. 12). In one embodiment detailed in FIG. 15, the force gauge 206 may include a compression spring 210 that is bounded by a housing 212 that forms an indicator channel 214 bordered by a plurality of force indicia 216 (FIG. 13) that progress from a proximal end 218 of the housing 212 toward a distal end 220 of the housing 212.

At the proximal end 218 of the housing 212, the compression spring 210 may be bounded by a proximal retaining disk 228 disposed adjacent to an indicator disk 230. The indicator disk 230 may support an indicator nut 231 that is in communication with the indicator channel 214 of the housing 212, such that movement of the indicator disk 230 causes the indicator nut 231 to move within the indicator channel 214. At the distal end 220 of the housing 212, the compression spring 210 may be bounded by a distal retaining disk 232. A hook 222 may extend from its proximal end 224 affixed to the proximal retaining disk 228, through a center of the indicator disk 230, the compression spring 210, and the distal retaining disk 232, and out the distal end 220 of the housing 212 to its distal end 226, such that a distal translation of the hook 222 causes the proximal retaining disk 228 to distally translate the indicator disk 230, which compresses the spring 210 distally and registers a proportionate tension force measurement or reading between the indicator nut 231 and the force indicia 216, thereby reflecting the tension force placed upon the hook 222.

The hook 222 may be translated distally either by a distal tension force applied to the distal end 226 of the hook 222 or by an opposite proximal tension force placed on a handle 234 affixed to the proximal end 218 of the housing 212, which translates the tensioner cradle assembly 202 rearward, or proximally, relative to the hook 222 and the compression spring 210. Notably, the hook 222 may take any appropriate size, shape, type, and/or geometry that is suitable for the requisite tendon preparation and/or testing task or equipment/system setup and/or arrangement.

Figure 16:
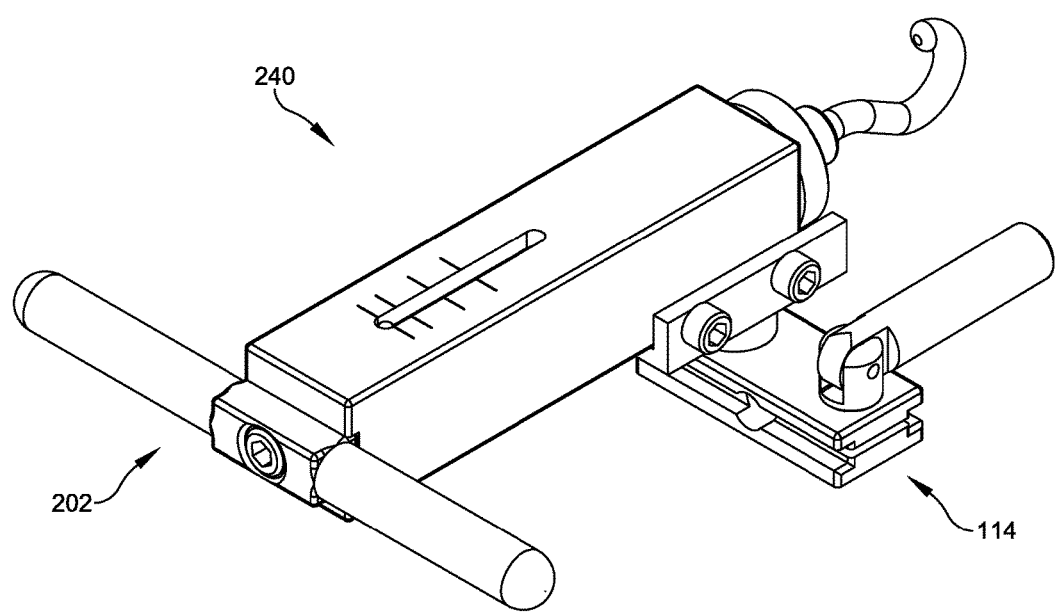
FIG. 16 illustrates a perspective view of one embodiment of a short tension-hook assembly for selectively securing to the triple-channel base of FIG. 1.

FIG. 16 illustrates a perspective view of one embodiment of a short tension-hook assembly 240. In this embodiment, the short tension-hook assembly 240 may be similar to the tall tension-hook assembly 200, but may exclude the post 204 such that the tensioner cradle assembly 202 is affixed directly to the locking-base assembly 114, thereby configuring the tensioner cradle assembly 202 in a lower position adjacent the triple-channel base 100 during use.

Figure 17:
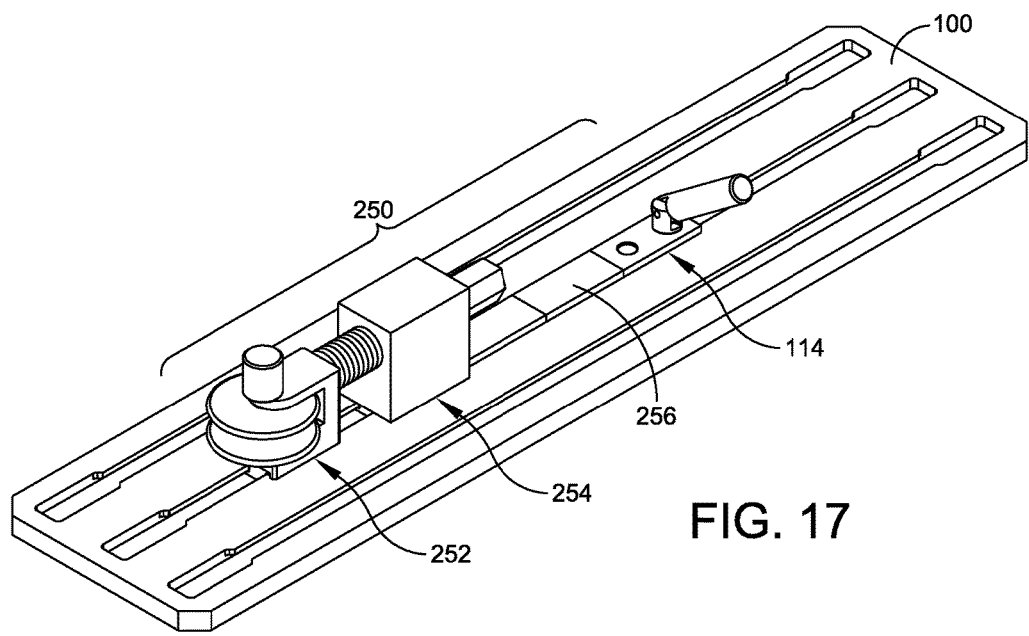
FIG. 17 illustrates a perspective view of one embodiment of a pulley tension assembly selectively secured to the triple-channel base of FIG. 1.

FIG. 17 illustrates a perspective view of one embodiment of a pulley tension assembly 250 as secured within the second channel 104 of the triple-channel base 100. In this embodiment, the pulley tension assembly 250 may include several adjacent assemblies that work together, including a pulley assembly 252, a pusher assembly 254, one or more sliders 256, and the locking-base assembly 114 detailed above in relation to FIGS. 4-5.

Figure 18:
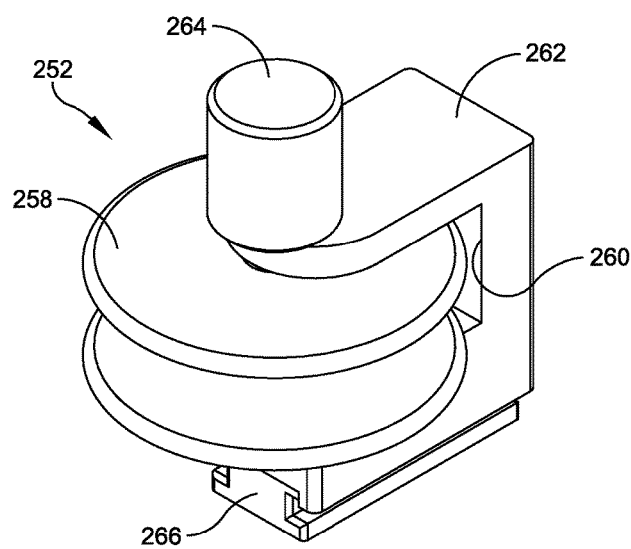
FIG. 18 illustrates a perspective view of one embodiment of a pulley assembly of the pulley tension assembly of FIG. 17.

FIG. 18 provides a perspective view of one embodiment of the pulley assembly 252. In this embodiment, the pulley assembly 252 may include a pulley 258 rotatively installed within a u-channel 260 of a u-block 262 via a pulley pin 264. The u-block 262 may be fastened upon or otherwise affixed to a mounting block 266, detailed in FIG. 19.

The mounting block 266 may be similar in form to the lock base 116 of the locking-base assembly 114, and may form a c-channel 268 along each longitudinal side, thereby enabling the attached pulley block 262 and the associated pulley 258 to glide along or within the longitudinal channels 102, 104, 106 of the triple-channel base 100 to a desired longitudinal position. The mounting block 266 may also include one or more threaded mounting apertures 269 for mounting accessory components thereupon.

Figure 19:
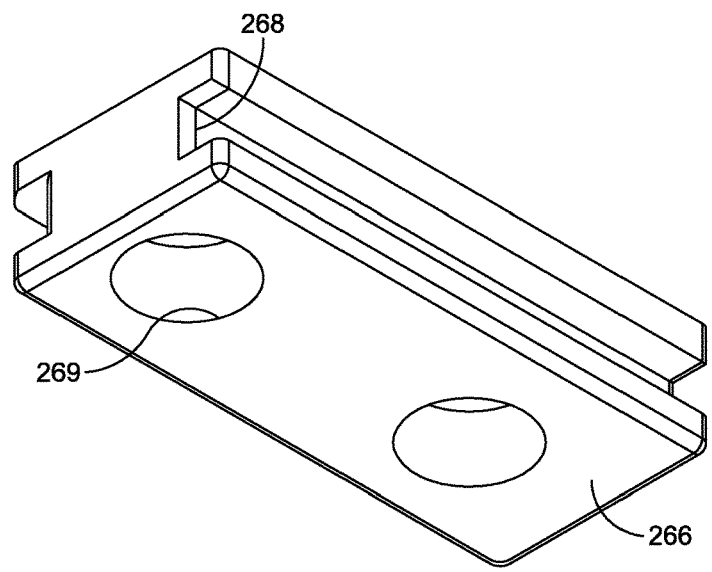
FIG. 19 illustrates a perspective view of one embodiment of a mounting block of the pulley assembly of FIG. 18.
Figure 20:
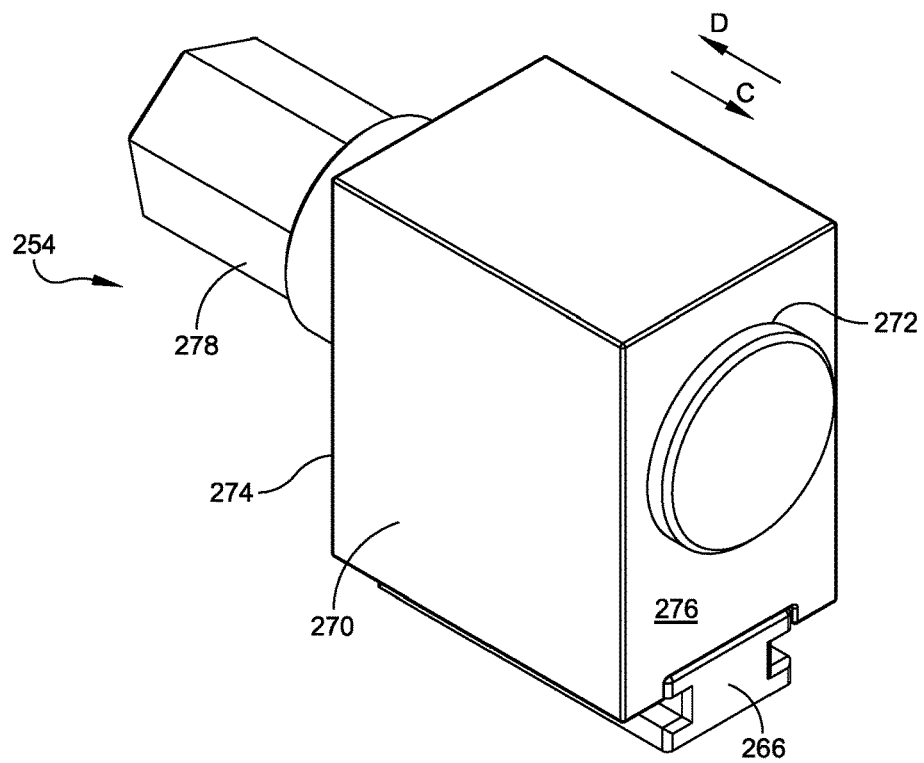
FIG. 20 illustrates a perspective view of one embodiment of a pusher assembly of the pulley tension assembly of FIG. 17.

FIG. 20 illustrates a perspective view of one embodiment of the pusher assembly 254 for positioning adjacent to the pulley assembly when the pulley tension assembly is in operation upon the triple-channel base 100, as shown in FIG. 17. In this embodiment, the pusher assembly 254 may include a pusher block 270 fastened upon or otherwise affixed to the mounting block 266 via the mounting apertures 269 (FIG. 19). The pusher block 270 may include a threaded aperture 272 that extends across the block 270 from a proximal end 274 to a distal end 276. A threaded pusher 278 may threadably engage with the threaded aperture 272 such that rotating the pusher 278 in a first direction advances the pusher 278 distally in the direction of arrow C and rotating the pusher 278 in a second direction causes the pusher to retreat proximally in the direction of arrow D.

Figure 21:
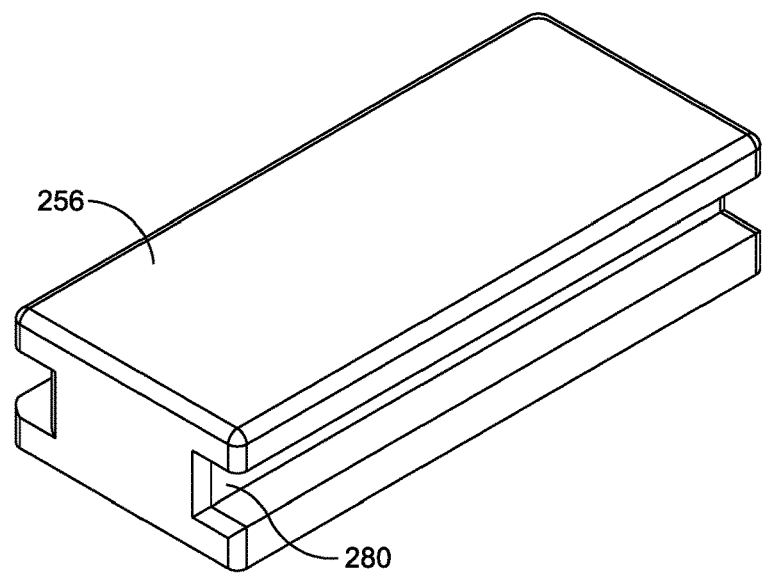
FIG. 21 illustrates a perspective view of one embodiment of a slider of the pulley tension assembly of FIG. 17.

One or more of the sliders 256, shown in FIG. 21, may separate the pusher assembly 254 from the locking-base assembly 114, as shown in FIG. 17. The slider 256 may have a form similar to the mounting block 266 and may form a c-channel 280 along each of its longitudinal sides to enable sliding along the channels 102, 104, 106 of the triple-channel base 100. In operation, as shown in FIG. 114, the slider or sliders 256 may be positioned between the pusher assembly 254 and the locking-base assembly 114 to provide clearance for the threaded pusher 278 in a retracted position in which the pusher 278 extends proximally from the threaded aperture 272 of the block 270 toward the locking-base assembly 114.

Figure 22:
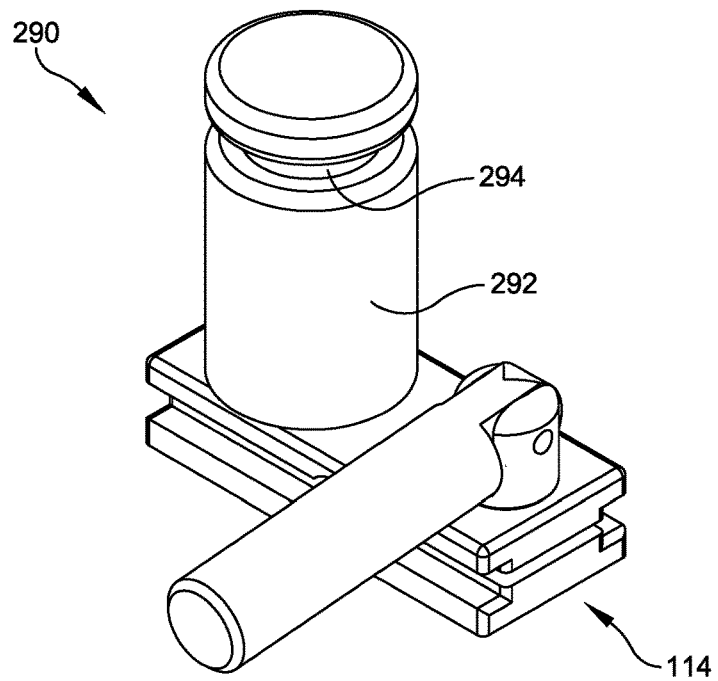
FIG. 22 illustrates a perspective view of one embodiment of a post assembly for selectively securing to the triple-channel base of FIG. 1.

FIG. 22 illustrates a perspective view of one embodiment of a post assembly 290. In this embodiment, the post assembly 290 may include a post 292 disposed upon and affixed to the locking-base assembly 114. A circumference of the post 292 may form a return channel 294 configured to act as a return or tie-off point for a suture or a tendon portion. The post 290 may have any appropriate height or diameter.

Each of the exemplary tendon-manipulation accessories discussed above in relation to FIGS. 4-22 may be formed of stainless steel, a sterilizable plastic, or a combination of both. The accessories may be machined by a metal fabrication technician, injection molded, or formed using any other appropriate fabrication technique.

As discussed above, the various tendon-manipulation accessories, including, for example, the holder assembly 140, the saddle assembly 150, the horizontal tendon-clamp assembly 160, the dual-direction tendon-clamp assembly 180, the tall tension-hook assembly 200, the short tension-hook assembly 240, the pulley tension assembly 250, and the post assembly 290 may be selectively positioned upon the first, the second, and the third channels 102, 104, 106 of the triple-channel base 100 in any number of custom arrangements depending on the steps required for preparing or manufacturing a pre-sutured tendon construct and/or for testing or pre-tensioning a prepared pre-sutured tendon construct of any type, length, tissue, and/or suturing method.

Figure 23A:
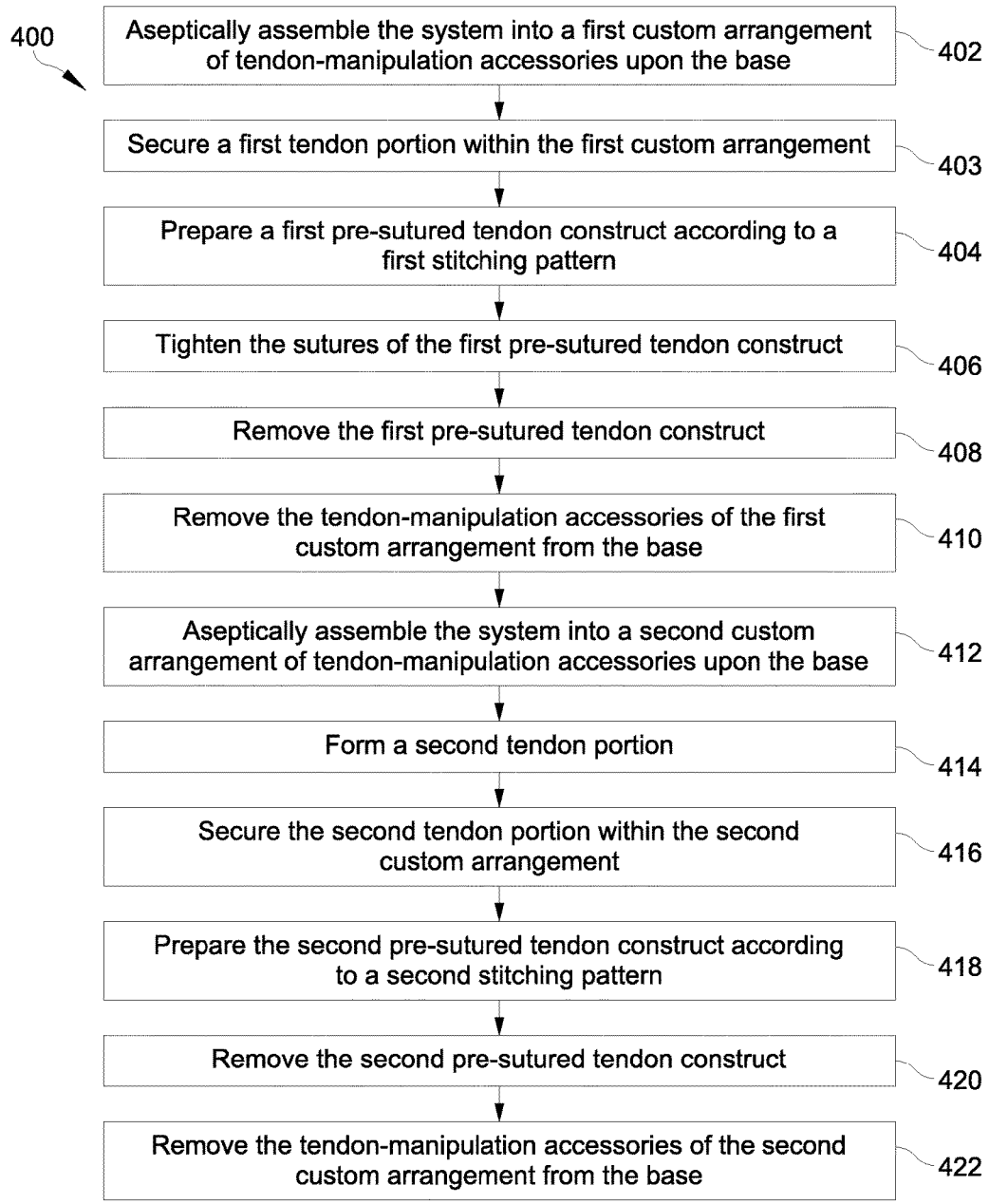
FIGS. 23A-23B provide a flowchart depicting an exemplary method of use for the system for preparing and testing pre-sutured tendon constructs shown in FIGS. 1-22.
Figure 23B:
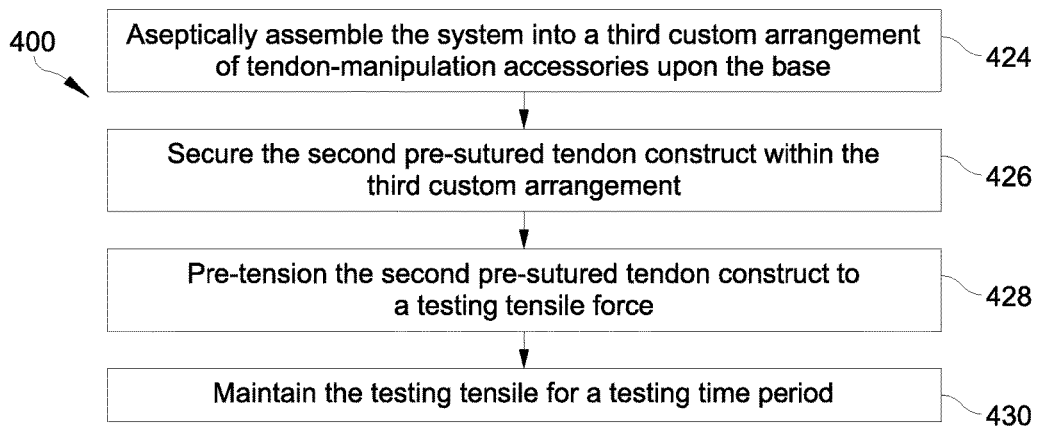
Figure 24:
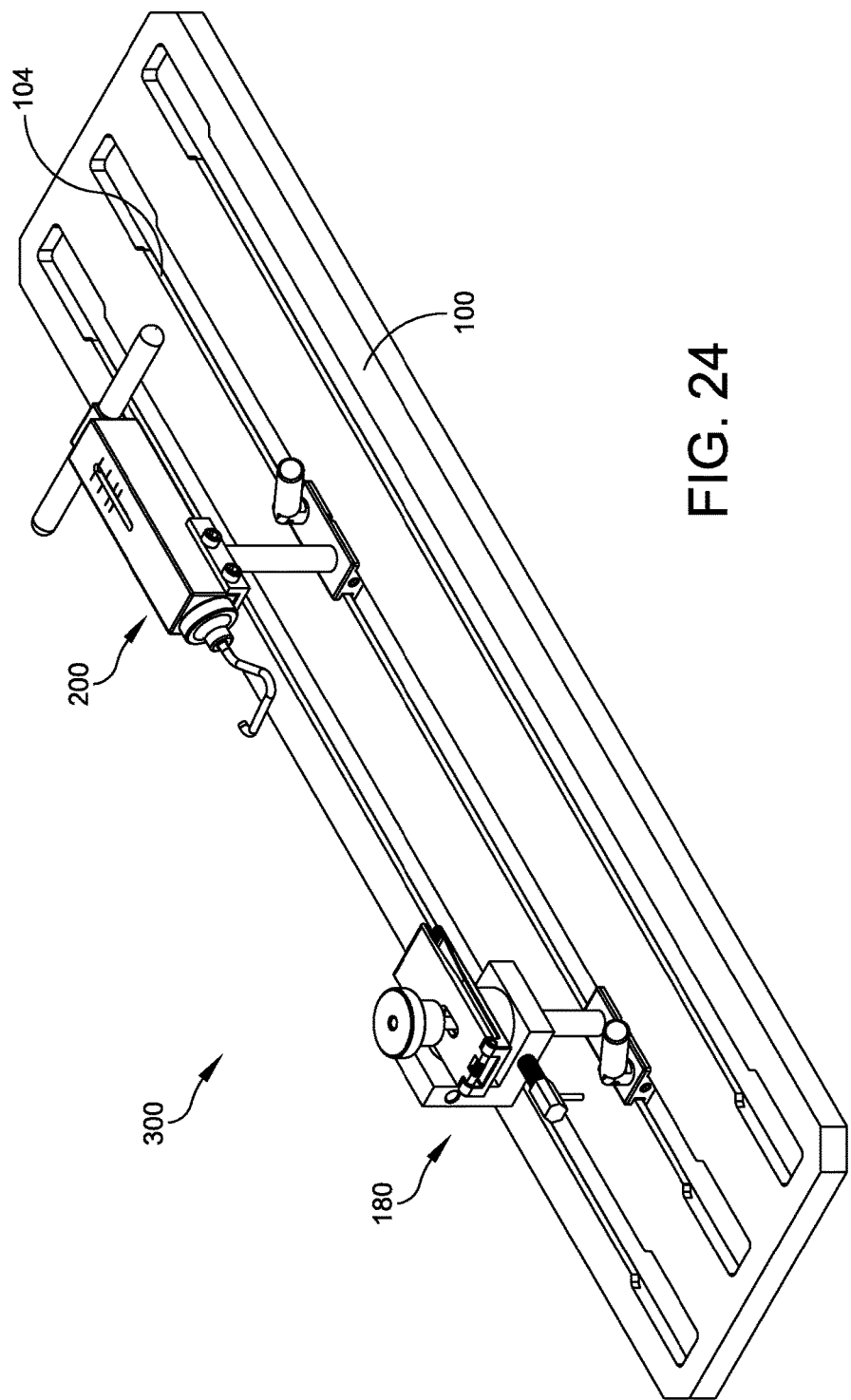
FIG. 24 illustrates a perspective view of a first custom arrangement of tendon-manipulation accessories upon the triple-channel base of FIG. 1.
Figure 25:
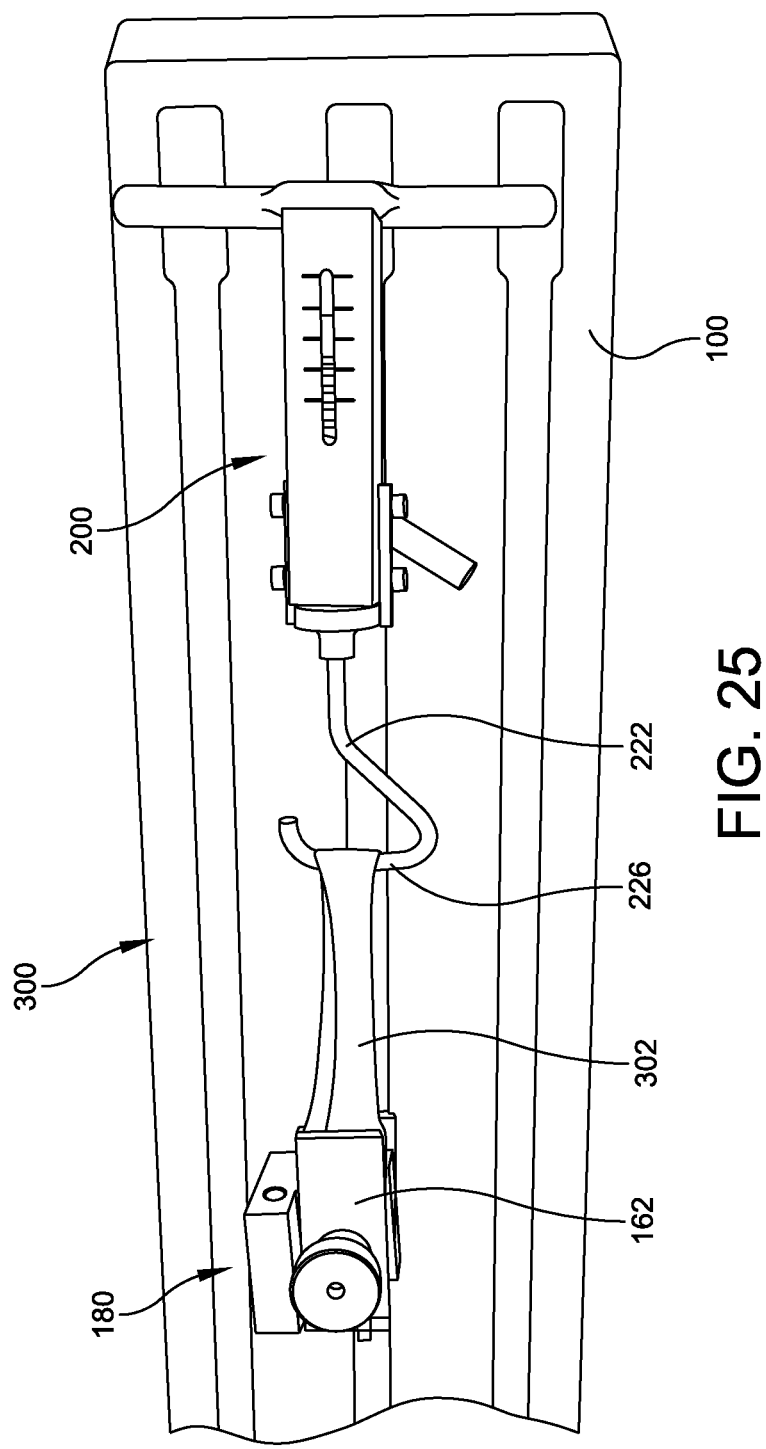
FIG. 25 illustrates a top view of the first custom arrangement of FIG. 24, securing a first tendon portion.
Figure 26:
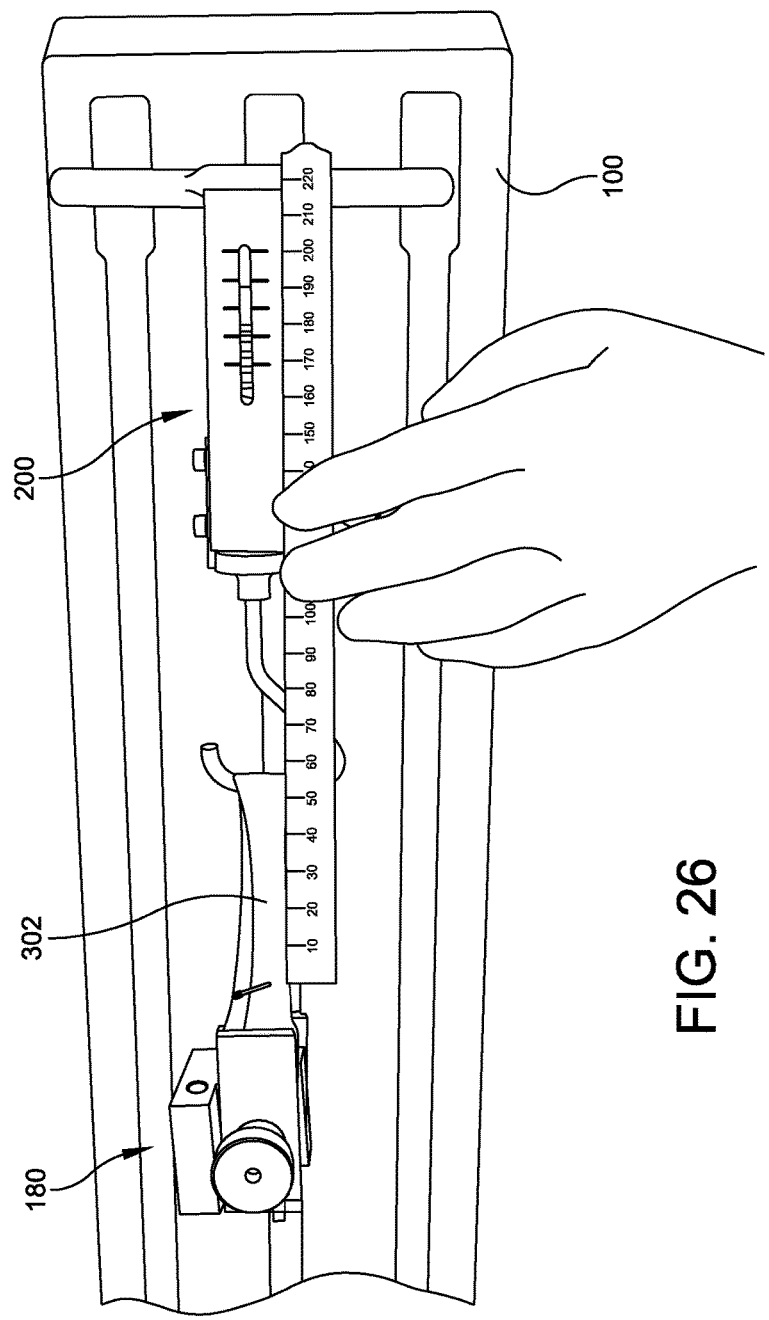
FIGS. 26-29 illustrate various steps in preparing/suturing a first pre-sutured tendon construct according to a first stitching pattern via the first custom arrangement of FIG. 24.
Figure 27:
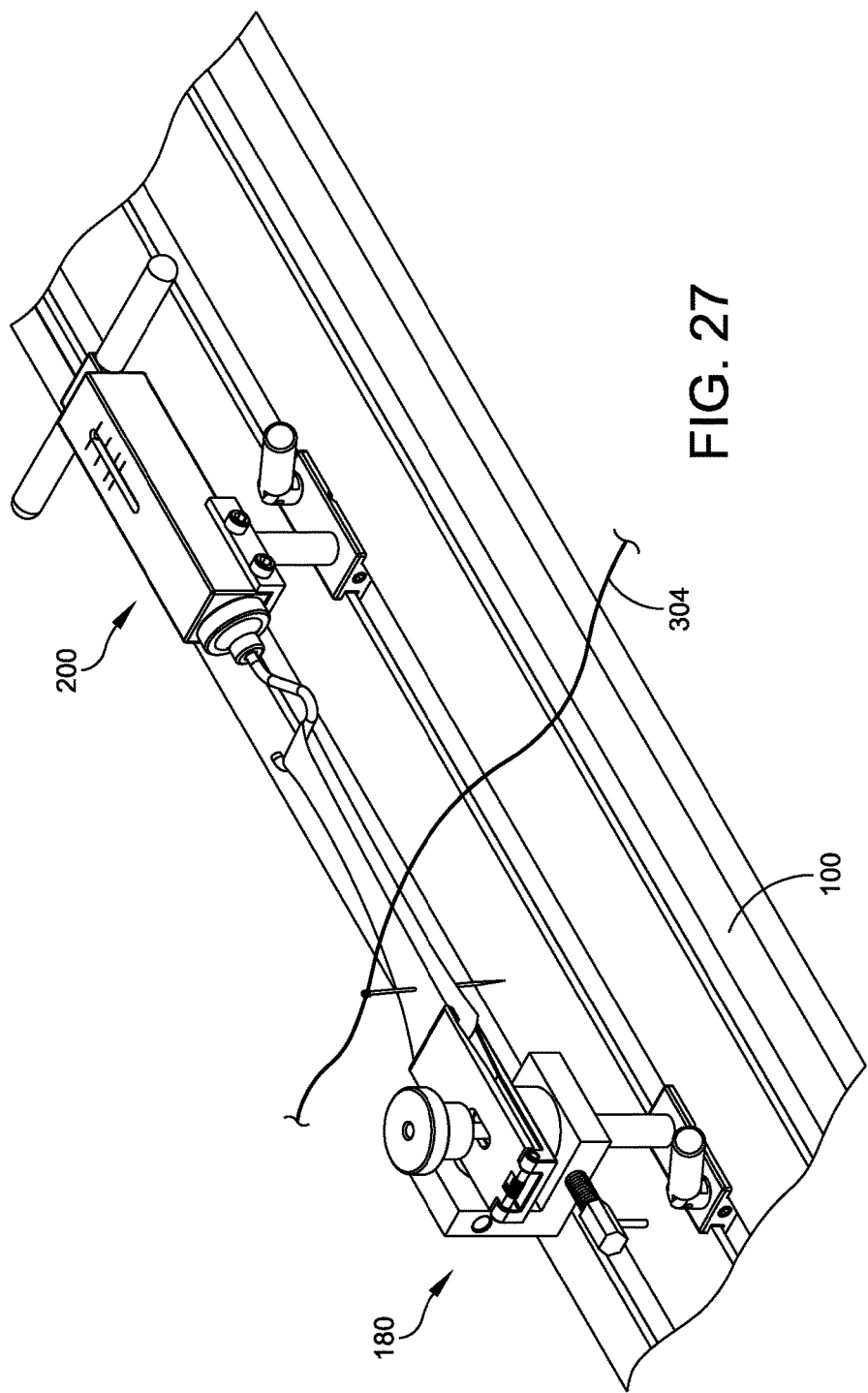
Figure 28:
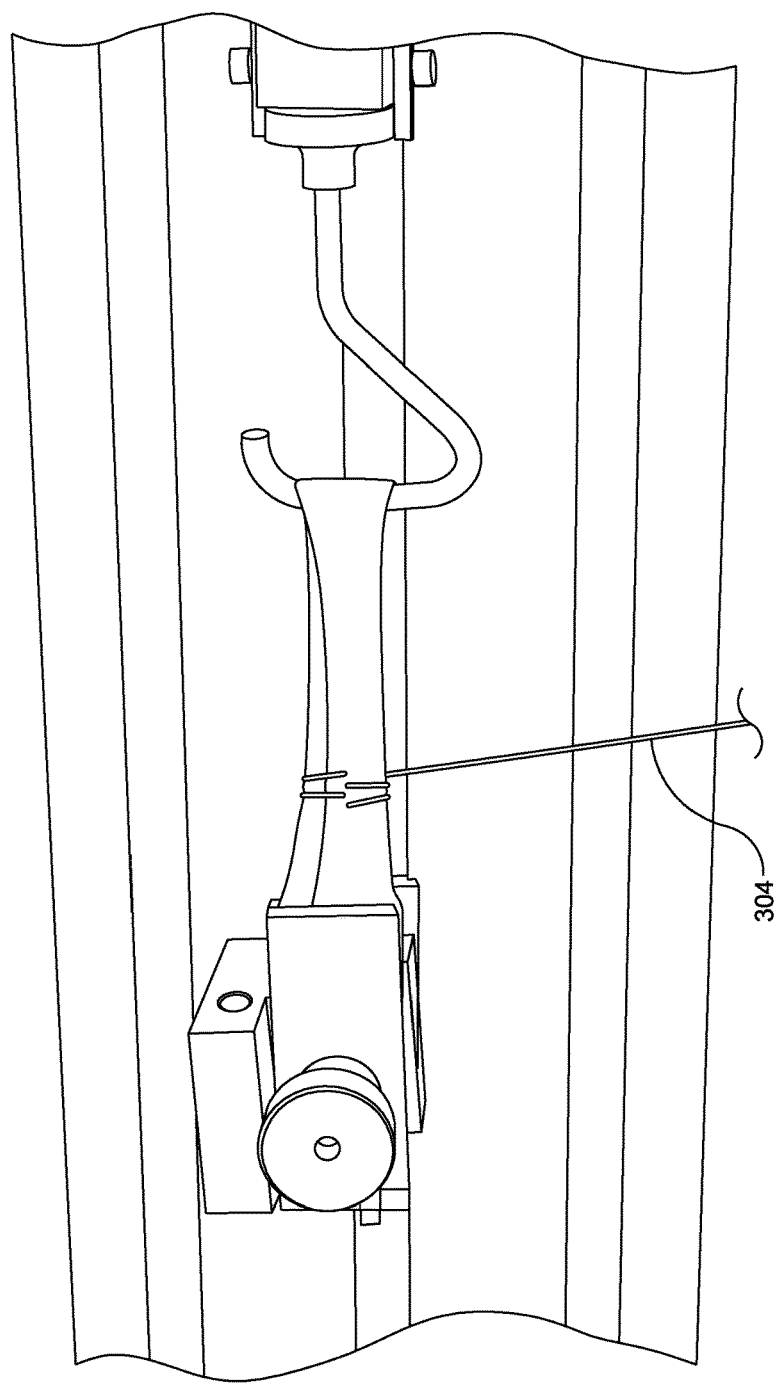
Figure 29:
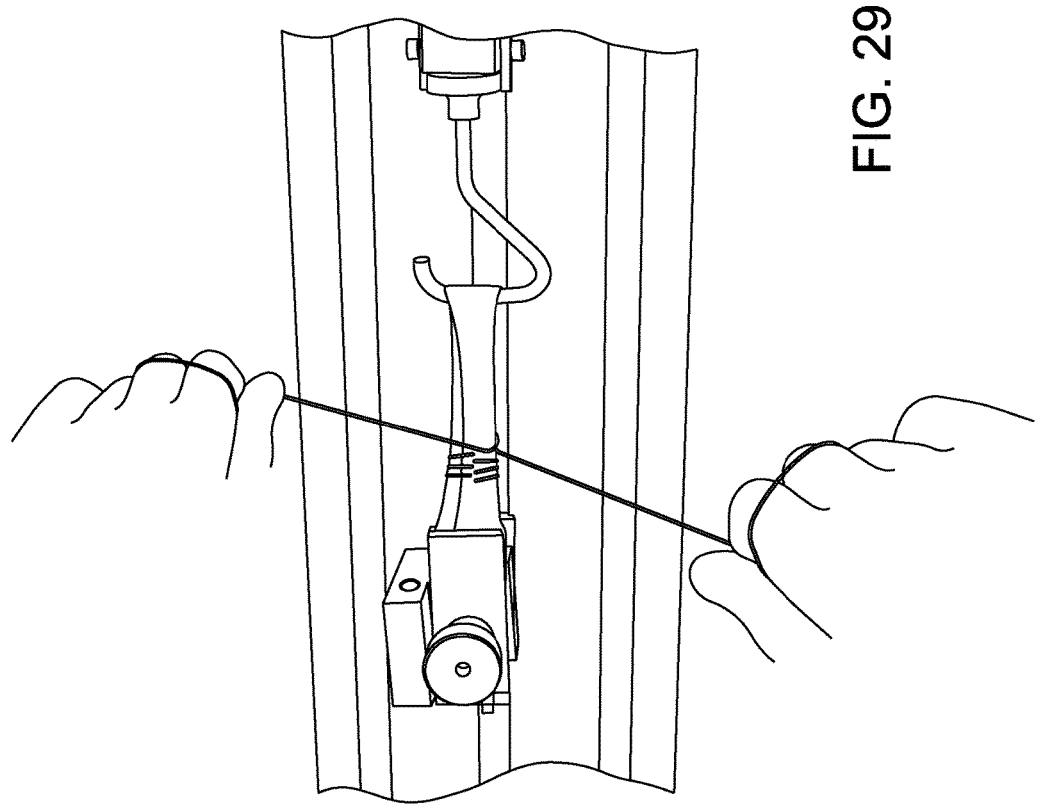

To provide an example, FIGS. 23A-23B provide a flowchart depicting an exemplary method of use (400) for the system described above, while FIGS. 24-40 illustrate individual steps of the method (400) in which the system is arranged and used in a number of custom arrangements for preparing and pre-tensioning pre-sutured tendon constructs. The method (400) begins when a technician or other operator aseptically assembles the customizable pre-sutured construct system into a first custom arrangement 300 (402), shown in FIG. 24. In the first custom arrangement 300, two of the tendon-manipulation accessories, namely the dual-direction tendon-clamp assembly 180 and the tall tension-hook assembly 200, may be positioned at first and second longitudinal positions within the second channel 104 of the base 100, respectively. Next, and in this particular custom arrangement 300, the technician may secure a first tendon portion 302 between the two tendon-manipulation accessories of the first custom arrangement 300 (403) by halving and stretching the first tendon portion 302 about the distal end 226 of the hook 222 of the tall tension-hook assembly 200 and capturing or clamping the free ends of the first tendon portion 302 within the upper and the lower jaws 162, 166 of the dual-direction tension-clamp assembly 180 in the horizontal configuration, as shown in FIG. 25.

Once the first tendon portion 302 is secured (403), the technician may use a first suture segment 304 to pre-suture the first tendon portion 302 in a first stitching pattern according to any appropriate suture method to prepare a first or initial tendon construct 306 (404), as shown in FIGS. 26-30. For example, in one embodiment, the technician may prepare the first tendon construct 306 according to the whip-stitching pattern and associated methods described in U.S. Pat. No. 9,504,557.

Figure 30:
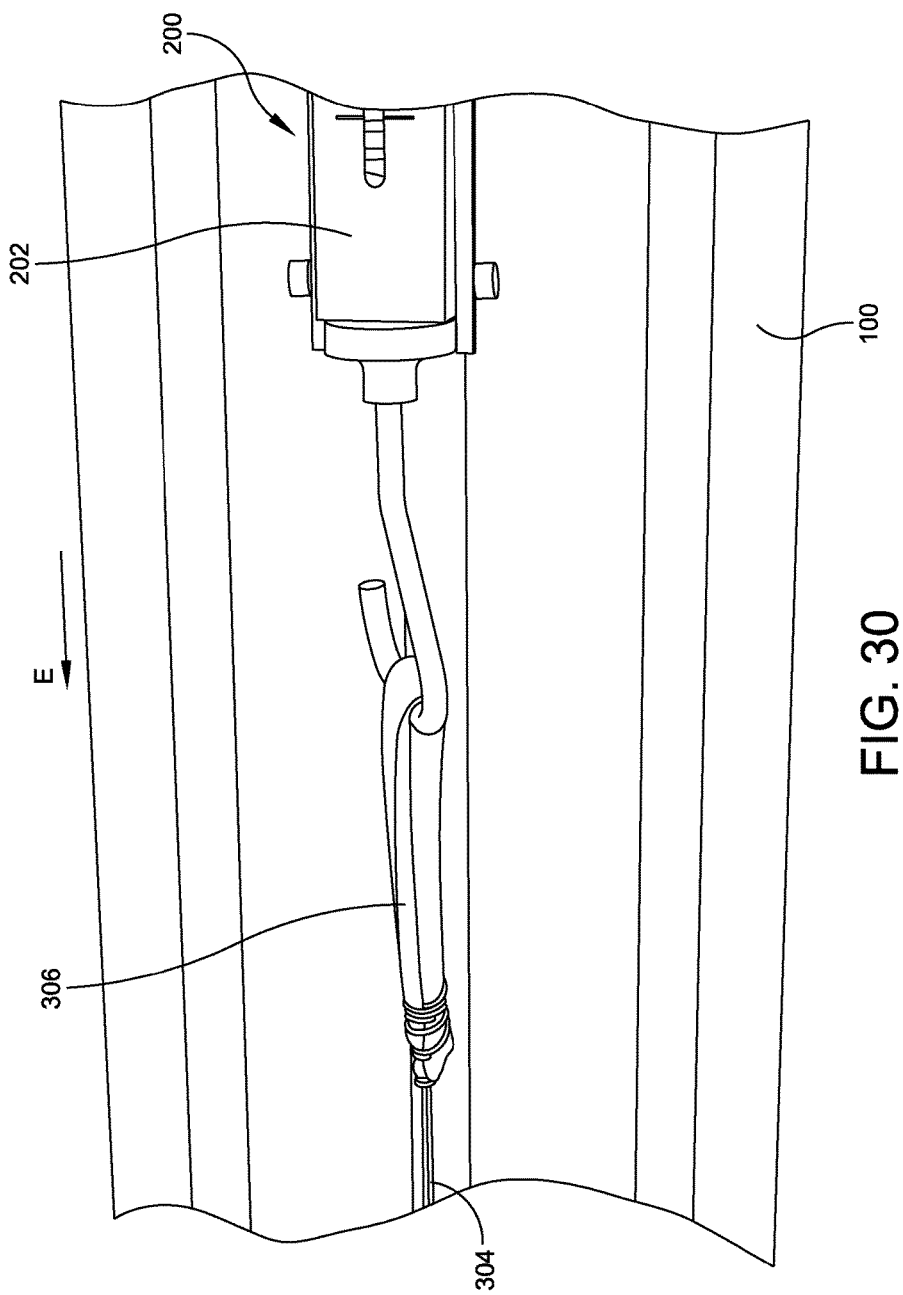
FIG. 30 illustrates the step of tightening the suture of the first pre-sutured tendon construct of FIGS. 26-29.

After the initial tendon construct 306 has been pre-sutured (404), the technician may tighten the sutures (406) by pulling the ends of the first suture segment 304 distally in the direction of arrow E, thereby distally translating the hook 222 of the tall tension-hook assembly 200, until a first tension force (e.g., 5-10 lbs.) registers on the force gauge 202, as shown in FIG. 30.

Figure 31:
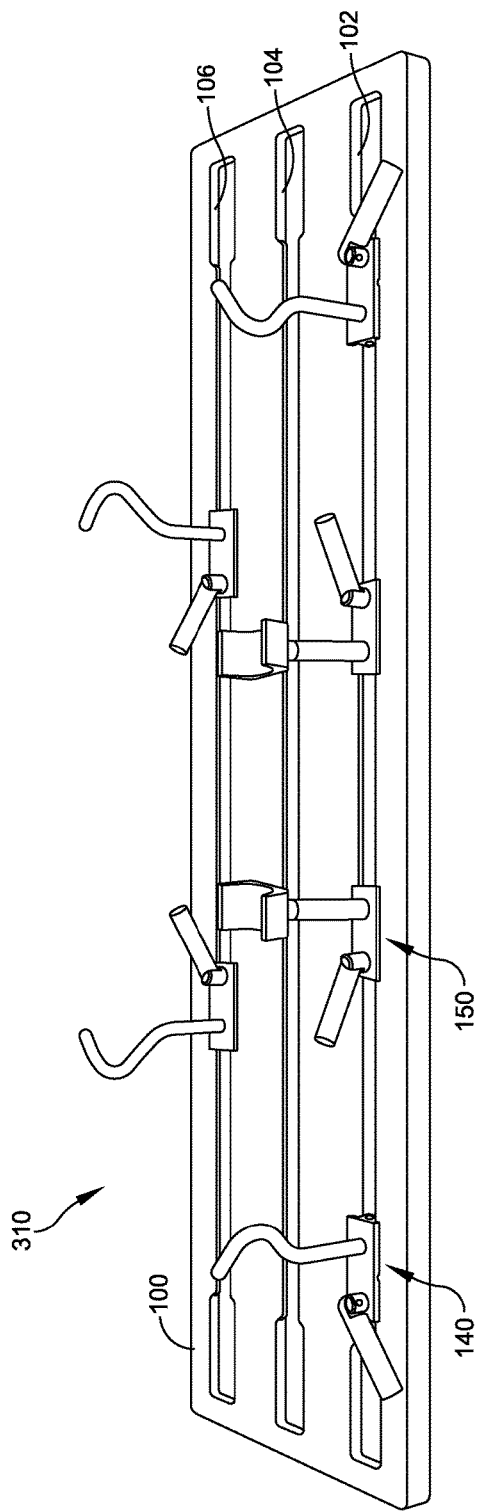
FIG. 31 illustrates a perspective view of a second custom arrangement of tendon-manipulation accessories upon the triple-channel base of FIG. 1.

After preparation and tensioning of the first or initial tendon construct 306 (404, 406), the technician may remove the initial tendon construct 306 from the first custom arrangement 300 (408) and remove the tendon-manipulation accessories of the first custom arrangement 300 from the base 100 (410) before aseptically assembling the system into a second custom arrangement 310 (412), shown in FIG. 31, configured for preparing a second or a "quad" construct 312 (FIG. 37) by securing two opposing saddle assemblies 150 and four opposing holder assemblies 140 in an offset pattern across the first and the third channels 102, 106 of the base.

Figure 32:
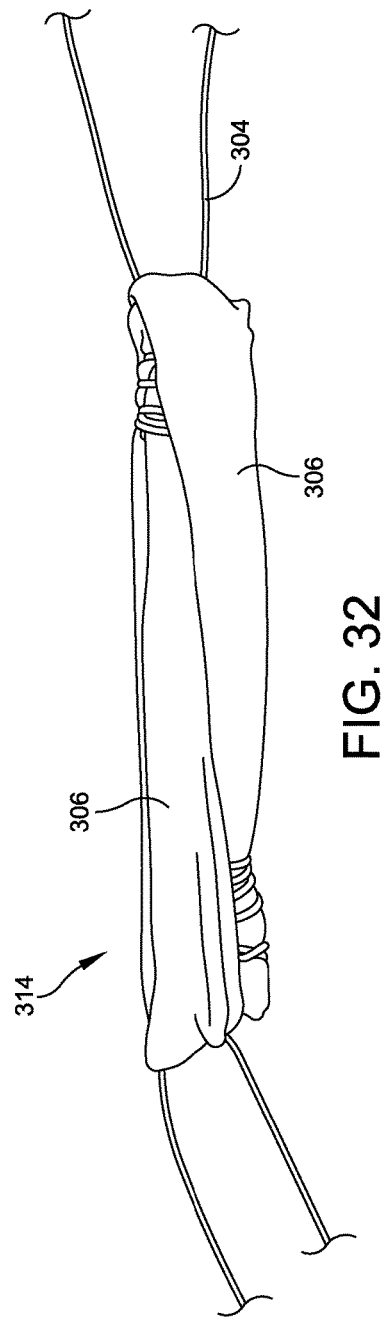
FIG. 32 illustrates a perspective view of an exemplary second tendon portion for securement within the second custom arrangement of FIG. 31.
Figure 33:
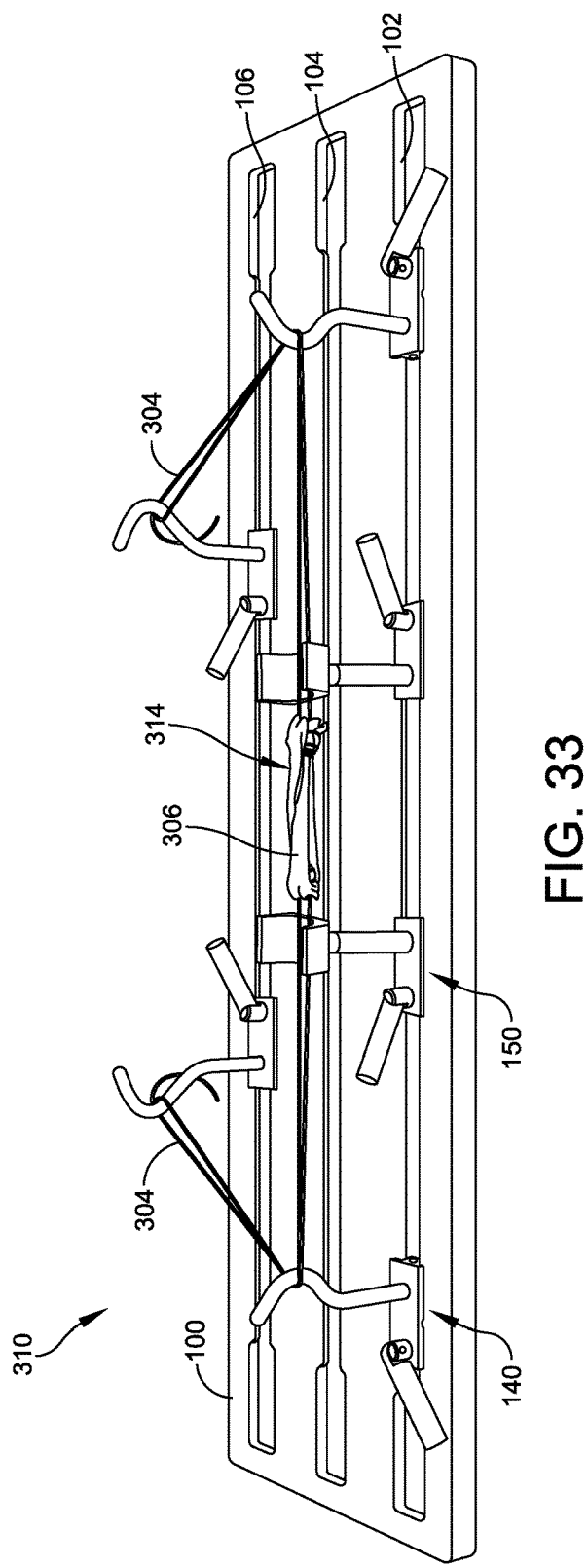
FIG. 33 illustrates the second custom arrangement of FIG. 31, securing the second tendon portion of FIG. 32.
Figure 34:
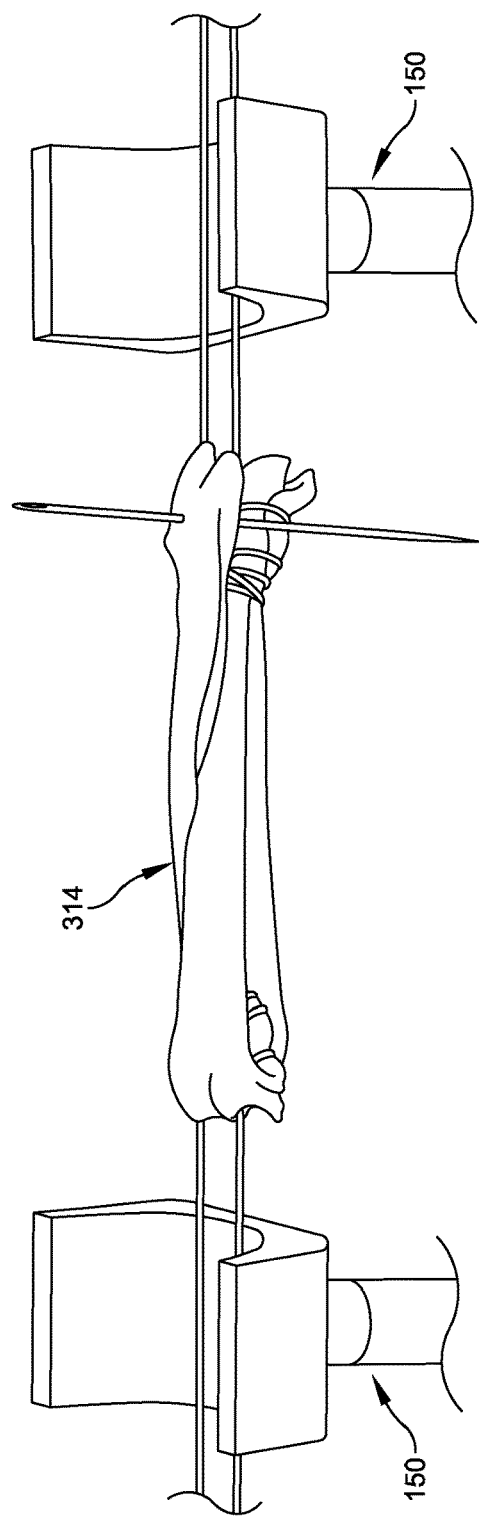
FIGS. 34-37 illustrate various steps of suturing/preparing a second pre-sutured tendon construct according to a second stitching pattern via the second custom arrangement of FIG. 31.
Figure 35:
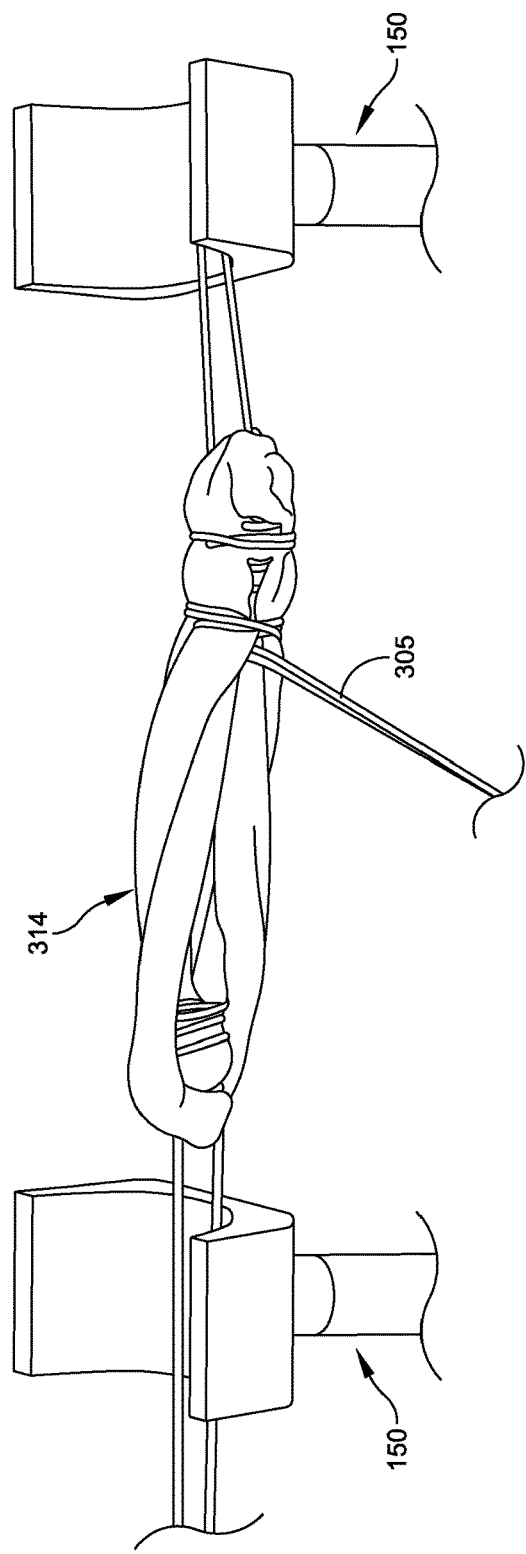
Figure 36:
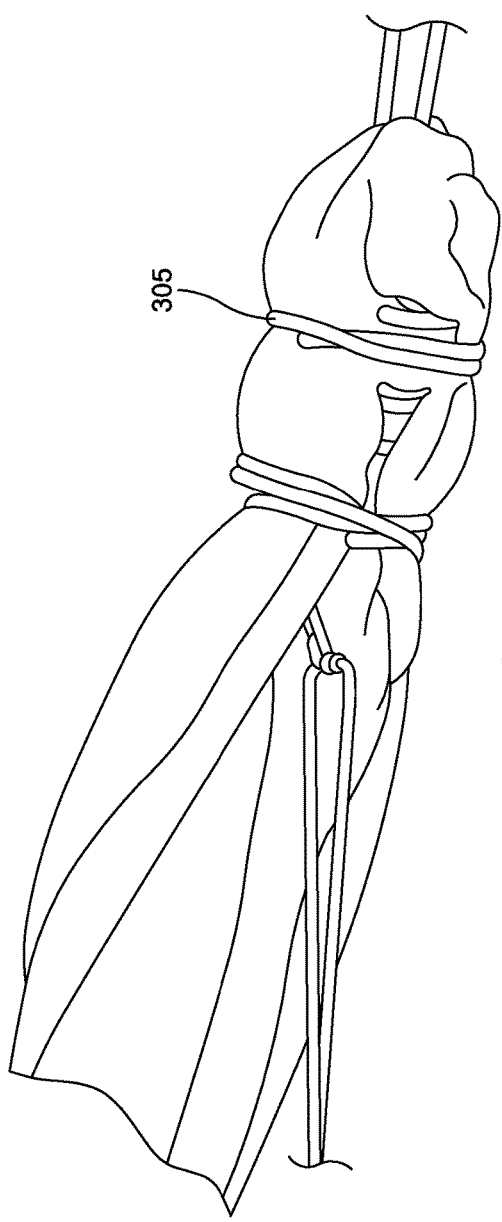
Figure 37:
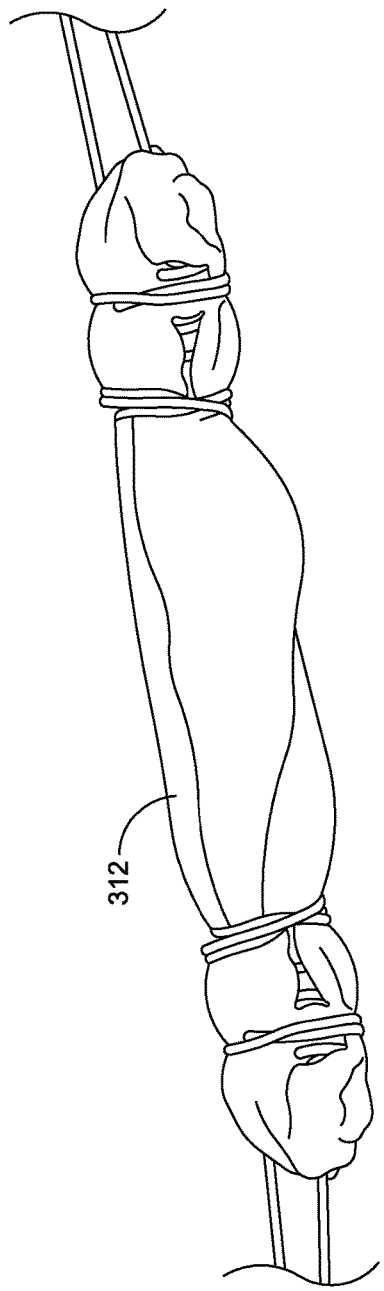

A second tendon portion 314 may be formed (414) by joining or overlapping two of the first or the initial pre-sutured constructs 306, as shown in FIG. 32. The operator may then stretch or secure the second tendon portion 314 to the second custom arrangement 310 (416) by securing the second tendon portion 314 between the two saddle assemblies 150 and leveraging the free ends of the first suture segments 304 against the holder assemblies 140, as shown in FIG. 33, before preparing the second or the "quad" pre-sutured tendon construct 312 (418) by using a second suture segment 305 to suture the second tendon portion 314 in a second stitching pattern according to any appropriate suture method, as shown in FIGS. 34-37.

Figure 38:
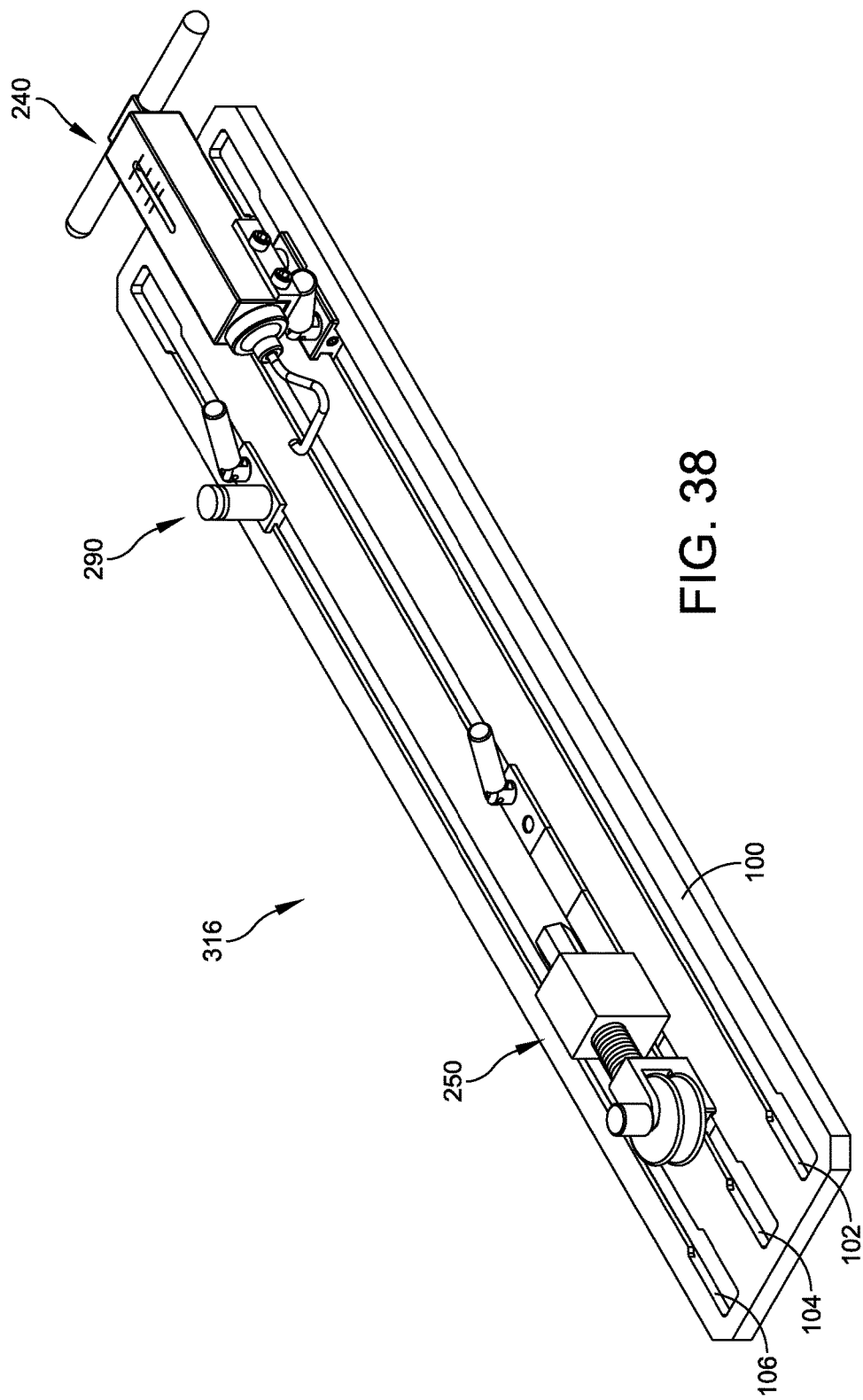
FIG. 38 illustrates a perspective view of a third custom arrangement of tendon-manipulation accessories upon the triple-channel base of FIG. 1.

After preparation of the second pre-sutured tendon construct 312 (418), the operator may remove the second pre-sutured tendon construct 312 from the second custom arrangement 310 (420), and remove the tendon-manipulation accessories of the second custom arrangement 310 from the base 100 (422), before aseptically assembling the system into a third custom arrangement 316 (424) suitable for testing or pre-tensioning the second pre-sutured tendon construct 312. As shown in FIG. 38, the third custom arrangement 316 may include the pulley tension assembly 250 secured at a first longitudinal position within the second channel 104, the short tension-hook assembly 240 secured at a second longitudinal position within the first channel 106, and the post assembly 290 secured at the second longitudinal position within the third channel 106 of the base 100. Once the third custom arrangement 316 is assembled (424), the technician may secure the second pre-sutured tendon construct 312 about the pulley 258 (426) such that the free ends of the first suture segment 304 are secured about the return channel 294 of the post 292 of the post assembly 290 and the hook 226 of the short tension-hook assembly 240, as shown in FIG. 39.

Figure 39:
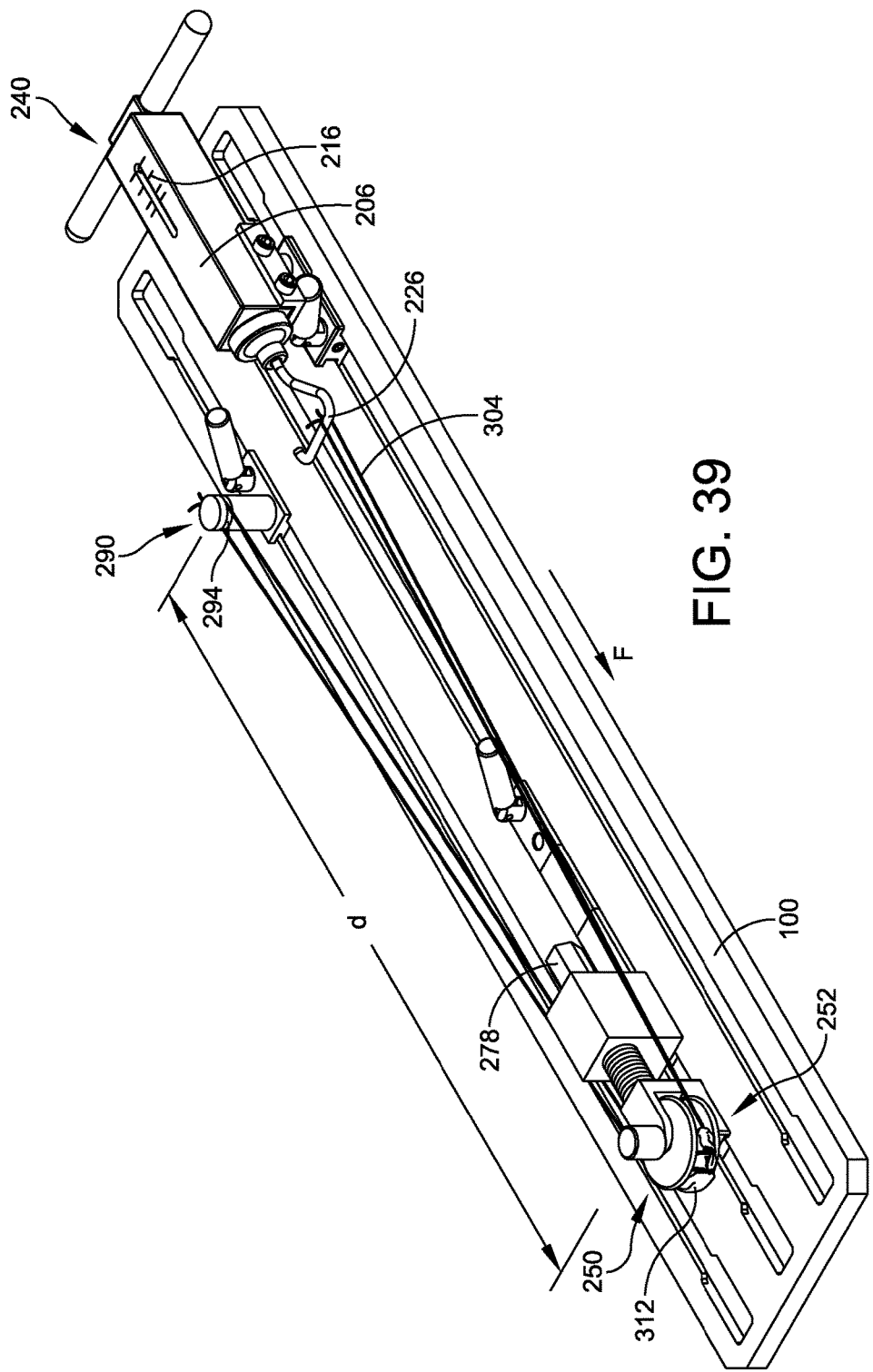
FIGS. 39-40 illustrate a perspective views of the second pre-sutured tendon construct of FIGS. 34-37 undergoing pre-tension testing via the third custom arrangement of FIG. 38.
Figure 40:
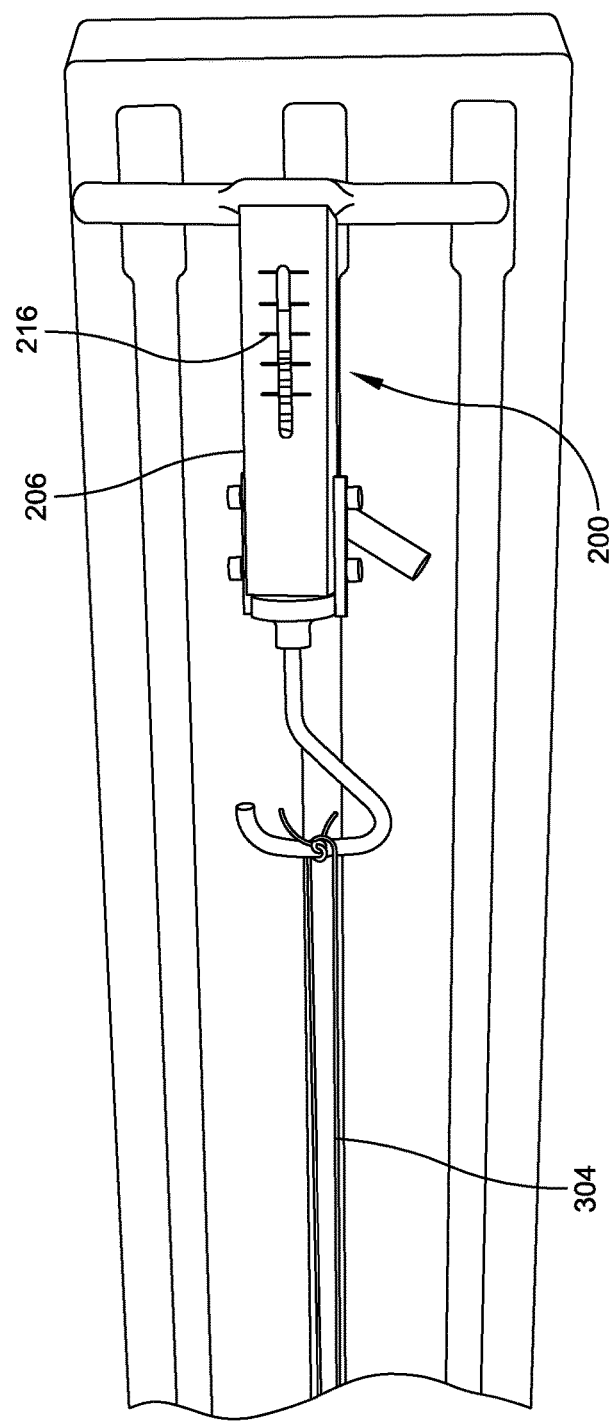

To pre-tension the second pre-sutured tendon construct 312 (428), the operator may rotate the threaded pusher 278 of the pulley tension assembly 250 such that the pusher 278 advances distally in the direction of arrow F, as shown in FIG. 39, thereby causing the pulley assembly 252 to translate distally in the direction of arrow F and increase a distance, d, between the first and the second longitudinal positions along the base 100. This incremental movement places the second pre-sutured tendon construct 312 in tension and translates the hook 226 of the short tension-hook assembly 240 distally, registering a proportional tension force on the indicia 216 of the hook-actuated force gauge 206, as shown in FIG. 40. The operator may use the pusher 278 to translate the pulley assembly 252 distally until a desired testing tensile force is achieved (e.g., 25 lbs.). The testing tensile force may be held for a testing time period (e.g., 5 minutes) to ensure the integrity of the second pre-sutured tendon construct 312 (430).

Figure 41:
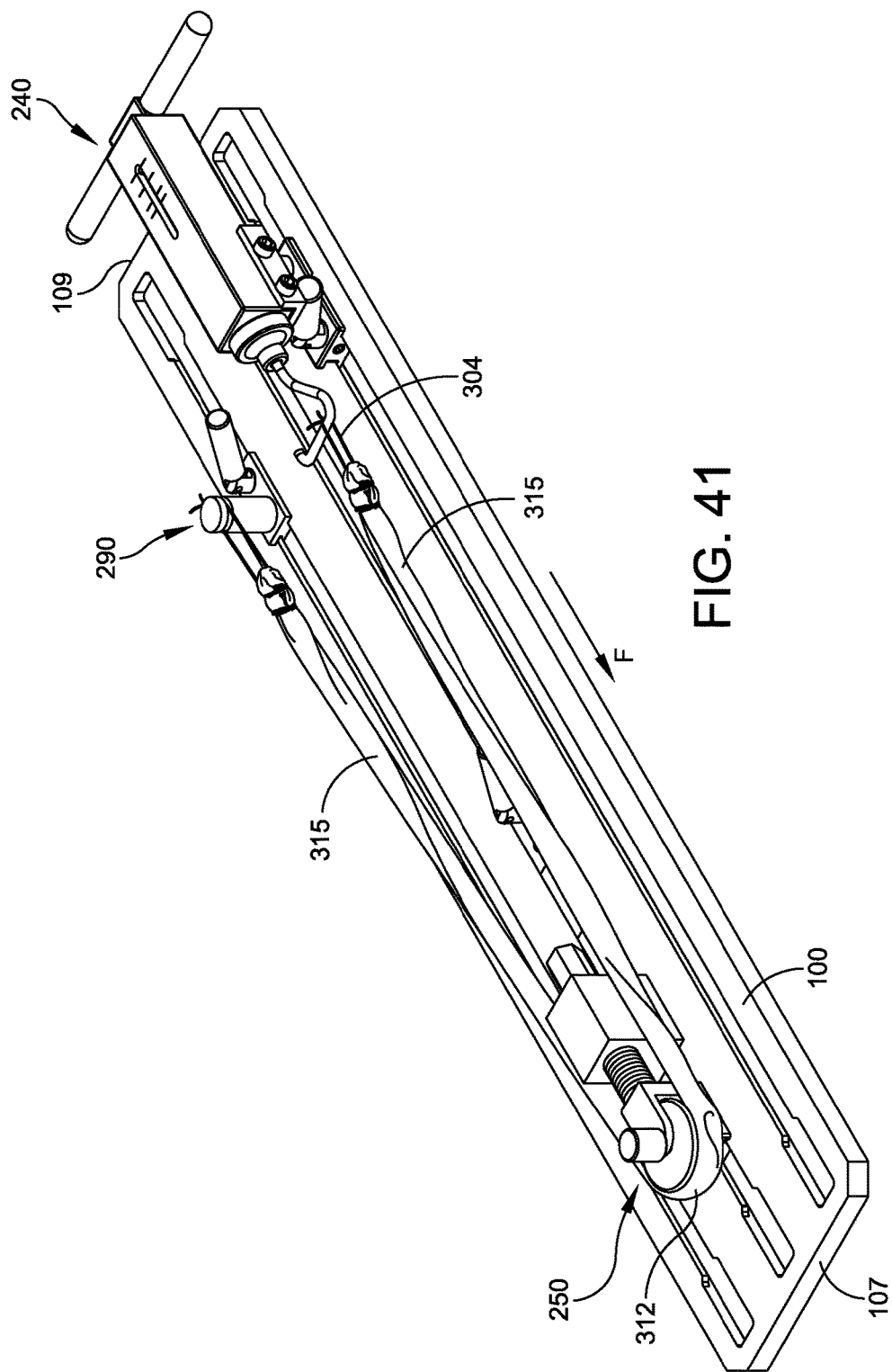
FIG. 41 illustrates a perspective view of a third pre-sutured tendon construct undergoing pre-tension testing via the third custom arrangement of FIG. 38.

Notably, in the third custom arrangement 316, and in any number of other custom arrangements for either preparing or testing pre-sutured constructs, the system may accommodate either a tissue portion (for preparation) or a pre-sutured tissue construct (for testing), such as construct 315, having a length that is up to double (2×) a length of the base 100 between the first and the second ends 107, 109, as shown in FIG. 41. As a result, the base 100 is spatially compact within the limited clean room environment, fits within traditional sterilization equipment, and requires less material to manufacture.

While three custom arrangements are described in the method (400) discussed herein, it should be noted that the steps and the custom arrangements discussed above are exemplary and included for explanatory purposes only. The tendon-manipulation accessories of FIGS. 4-22 are intended to be arranged and secured upon the base 100 in any useful custom arrangement that is suitable for pure-sutured construct preparation and/or testing, allowing the system described herein to accommodate multiple pre-sutured construct preparation and/or testing methods with a single, customizable set of tools. The system, including the base 100 and the various tendon-manipulation accessories, may be sterilized as necessary between custom arrangements.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A customizable system for manufacturing and testing a pre-sutured tendon construct, comprising:
    a base having first, second, and third longitudinal channels extending between first and second ends of the base; and
    a plurality of tendon-manipulation accessories, each having a locking base assembly for selectively securing each of the tendon-manipulation accessories along one of the first, the second, or the third longitudinal channels so as to configure two or more of the tendon-manipulation accessories in two or more custom arrangements suitable for each of preparing the pre-sutured tendon construct and pre-tensioning the pre-sutured tendon construct.

2. The customizable system of claim 1, wherein the plurality of the tendon-manipulation accessories comprise at least one or more holder assemblies, one or more saddle assemblies, one or more tendon-clamp assemblies, one or more tall tension-hook assemblies, one or more short tension-hook assemblies, one or more pulley-tension assemblies, and one or more post assemblies.

3. The customizable system of claim 1, wherein the two or more of the custom arrangements comprise a first custom arrangement suitable for preparing a first pre-sutured tendon construct, the first custom arrangement comprising a tendon-clamp assembly secured at a first longitudinal position and a tall tension-hook assembly secured at a second longitudinal position within a select one of the first, the second, or the third longitudinal channels of the base, the tendon-clamp assembly and the tall tension-hook assembly each positioned so as to stretch a tendon portion therebetween.

4. The customizable system of claim 3, wherein the two or more of the custom arrangements further comprise a second custom arrangement suitable for preparing a second pre-sutured tendon construct, the second custom arrangement comprising:
    first and second opposing saddle assemblies secured within the first channel;
    first and second opposing holder assemblies secured within the first channel, the first and the second holder assemblies outwardly bounding the first and the second saddle assemblies; and
    third and fourth opposing holder assemblies secured within the third channel, the first, the second, the third, and the fourth holder assemblies positioned so as to stretch the first pre-sutured tendon construct between the first and the second saddle assemblies.

5. The customizable system of claim 4, wherein the two or more of the custom arrangements further comprise a third custom arrangement suitable for pre-tensioning the first or the second pre-sutured tendon construct, the third custom arrangement comprising:
    a short tension-hook assembly secured within the first channel;
    a pulley-tension assembly secured within the second channel, the pulley-tension assembly having a pulley; and
    a post assembly secured within the third channel, the short tension-hook assembly, the pulley-tension assembly, and the post assembly positioned longitudinally between the first and the second ends of the base so as to stretch the first or the second pre-sutured tendon construct around the pulley of the pulley-tension assembly at a testing tensile force.

6. The customizable system of claim 5, wherein a distance between the first and the second ends of the base is less than a length of the first pre-sutured tendon construct and less than a length of the second pre-sutured tendon construct.

7. The customizable system of claim 1, wherein the plurality of the tendon-manipulation accessories are configurable in a plurality of additional custom arrangements suitable for preparing a plurality of additional pre-sutured tendon constructs and for testing the plurality of the additional pre-sutured tendon constructs.

8. A soft-tissue construct preparation and testing tool, comprising:
 a triple-channel base extending longitudinally between a first end and a second end;
 a pulley-tension assembly having a pulley secured at a first longitudinal position within a second channel of the triple-channel base;
 a tension-hook assembly secured at a second longitudinal position within a first channel of the triple-channel base; and
 a post assembly secured at the second longitudinal position within a third channel of the triple-channel base, wherein:
  a pre-sutured soft-tissue construct extends from a first end attached to the post assembly, about the pulley of the pulley-tension assembly, to a second end attached to the tension-hook assembly;
  increasing a distance between the first and the second longitudinal positions increases a tension placed upon the pre-sutured soft-tissue construct and registers a proportional tension-force measurement on the tension-hook assembly; and
  a distance between the first and the second ends of the triple-channel base is less than a distance between the first and the second ends of the pre-sutured soft-tissue construct.

9. The soft-tissue construct preparation and testing tool of claim 8, wherein the post assembly comprises:
 a locking-base assembly configured to secure the post assembly at a plurality of longitudinal positions within the third channel of the triple-channel base; and
 a post extending upward from the locking-base assembly, the post configured to receive and retain a suture extending from the first end of the pre-sutured soft-tissue construct.

10. The soft-tissue construct preparation and testing tool of claim 8, wherein the tension-hook assembly comprises:
 a locking-base assembly configured to secure the tension-hook assembly at a plurality of longitudinal positions within the first channel of the triple-channel base; and
 a force gauge affixed to the locking-base assembly, the force gauge including:
  a compression spring bounded by a housing having an indicator channel marked by a progression of force indicia, an indicator positioned at a proximal end of the housing, and a retainer disk positioned at a distal end of the housing;
  a hook having a first end extending distally from the housing and a second end coupled with the indicator such that a distal translation of the hook compresses the compression spring and registers the proportional tension-force measurement between the indicator and the force indicia.

11. The soft-tissue construct preparation and testing tool of claim 8, wherein the pulley-tension assembly further comprises:
 a locking-base assembly configured to secure the pulley-tension assembly at a plurality of longitudinal positions within the second channel of the triple-channel base; and
 a pusher assembly disposed between the locking-base assembly and the pulley, the pusher assembly comprising:
  a mounting slidably engaged with the second channel;
  a pusher block affixed to the mounting, the pusher block having a threaded aperture extending from a proximal end adjacent the locking-base assembly to a distal end adjacent the pulley; and
  a pusher threadably engaged with the threaded aperture, wherein rotating the pusher in a first direction translates the pusher distally against the pulley, thereby incrementally increasing the distance between the first and the second longitudinal positions to incrementally increase the tension placed upon the pre-sutured soft-tissue construct and register the proportional tension-force measurement on the tension-hook assembly.

12. The soft-tissue construct preparation and testing tool of claim 11, the locking-base assembly including:
 a lock base having top and bottom plates separated by an offset; and
 a threaded swivel extending through the top and the bottom plates, wherein the top and the bottom plates move toward a closed position when the swivel is rotated in a first direction and toward an open position when the swivel is rotated in a second direction.

13. The soft-tissue construct preparation and testing tool of claim 8, wherein the distance between the first and the second ends of the triple-channel base is one-half or less of the distance between the first and the second ends of the pre-sutured soft-tissue construct.

14. The soft-tissue construct preparation and testing tool of claim 8, further comprising at least one or more holder assemblies, one or more saddle assemblies, one or more tendon-clamp assemblies, and one or more tall tension-hook assemblies, each of the holder assemblies, the saddle assemblies, the tendon-clamp assemblies, and the tall tension-hook assemblies selectively securable within the first, the second, and the third channels of the triple-channel base to form a plurality of custom arrangements, each suitable for one or both of preparing and testing a plurality of soft-tissue constructs.

15. A method of preparing and pre-tensioning a pre-sutured tendon construct, the method comprising:
 aseptically assembling a customizable pre-sutured construct system having a triple-channel base and a plurality of tendon-manipulation accessories into a first custom arrangement in which at least two of the tendon-manipulation accessories are secured upon the triple-channel base in a manner suitable for preparing a first pre-sutured tendon construct;
 securing a first tendon portion between the at least two tendon-manipulation accessories of the first custom arrangement;
 suturing the first tendon portion according to a first stitching pattern to form the first pre-sutured tendon construct;
 removing the first pre-sutured tendon construct from the first custom arrangement;
 removing the at least two tendon-manipulation accessories from the triple-channel base;
 aseptically assembling the customizable pre-sutured construct system into a second custom arrangement in which at least another two of the plurality of the tendon-manipulation accessories are secured upon the triple-channel base in a manner suitable for preparing a second pre-sutured tendon construct;

securing a second tendon portion between the at least another two of the plurality of the tendon-manipulation accessories of the second custom arrangement;

suturing the second tendon portion according to a second stitching pattern to form the second pre-sutured tendon construct; and removing the second pre-sutured tendon construct from the second custom arrangement.

16. The method of claim 15, further comprising:
aseptically assembling the customizable pre-sutured construct system into a third custom arrangement in which at least three of the plurality of the tendon-manipulation accessories are positioned upon the triple-channel base in a manner suitable for testing an integrity of the first pre-sutured tendon construct or the second pre-sutured tendon construct;

securing the first or the second pre-sutured tendon construct within the third custom arrangement of the at least three of the plurality of the tendon-manipulation accessories;

using at least one of the at least three of the tendon-manipulation accessories, tensioning the first or the second pre-sutured tendon construct to a testing tensile force; and recording the testing tensile force and a success or a failure of the first or the second pre-sutured tendon construct under the testing tensile force.

17. The method of claim 16, wherein the second pre-sutured tendon construct comprises a quad construct including two joined ones of the first pre-sutured tendon construct.

18. The method of claim 17, wherein:
the aseptically assembling the customizable pre-sutured construct system into the first custom arrangement comprises:
securing a tendon-clamp assembly at a first longitudinal position within one of a first channel, a second channel, and a third channel of the triple-channel base, the tendon-clamp assembly comprising hinged upper and lower jaws; and
disposing a tension-hook assembly opposite the tendon-clamp assembly at a second longitudinal position within the one of the first channel, the second channel, and the third channel of the triple-channel base, the tension-hook assembly comprising a hook configured to actuate a force gauge; and
the securing the tendon portion comprises:
folding the tendon portion in half to form a folded end and two free ends;
securing the free ends within the upper and the lower jaws of the tendon clamp assembly;
looping the folded end around the hook of the tension-hook assembly;
pulling the tension-hook assembly opposite the tendon-clamp assembly to tension the tendon portion until the force gauge indicates a first tension force; and
securing the tension-hook assembly within the one of the first, the second, and the third channels.

19. The method of claim 18, wherein:
the aseptically assembling the customizable pre-sutured construct system into the second custom arrangement comprises:
securing first and second opposing saddle assemblies within the first channel;
securing first and second opposing holder assemblies within the first channel, the first and the second holder assemblies outwardly bounding the first and the second saddle assemblies; and
securing third and fourth opposing holder assemblies within the third channel; and
the securing the second tendon portion comprises:
stretching the two joined ones of the first pre-sutured tendon construct between the first and the second saddle assemblies.

20. The method of claim 19, wherein:
the aseptically assembling the customizable pre-sutured construct system into the third custom arrangement comprises:
securing a short tension-hook assembly within the first channel;
securing a pulley-tension assembly within the second channel, the pulley-tension assembly having a pulley; and
securing a post assembly within the third channel, wherein the short tension-hook assembly, the pulley-tension assembly, and the post assembly are positioned longitudinally between the first and the second ends of the base so as to stretch the first or the second pre-sutured tendon construct around the pulley of the pulley-tension assembly to a testing tensile force.

* * * * *